United States Patent [19]

Casci

[11] Patent Number: 5,108,579
[45] Date of Patent: Apr. 28, 1992

[54] ZEOLITES

[75] Inventor: John L. Casci, Redcar, England

[73] Assignee: Imperial Chemical Industries PLC, London, England

[21] Appl. No.: 716,255

[22] Filed: Jun. 17, 1991

[30] Foreign Application Priority Data

Jun. 22, 1990 [GB] United Kingdom ............... 9013916

[51] Int. Cl.⁵ .................................... C10G 11/00
[52] U.S. Cl. .................................... 208/46; 208/110; 208/111; 208/112; 208/113; 208/108; 208/119; 208/120; 208/121; 208/122; 208/123; 208/134; 208/135; 585/407; 585/418; 585/420; 564/479; 564/480; 502/77; 423/328
[58] Field of Search ............... 208/46, 110-113, 208/108, 119-123, 134-135; 585/407, 418, 420; 564/479, 480; 502/77; 423/328, 329, 330

[56] References Cited

U.S. PATENT DOCUMENTS

| | | | |
|---|---|---|---|
| 4,490,342 | 12/1984 | Valyocsik | 423/328 |
| 4,537,754 | 8/1985 | Casci et al. | 423/328 |
| 4,557,919 | 12/1985 | Sumitani et al. | 423/328 |
| 4,741,891 | 5/1988 | Casci et al. | 423/328 |

FOREIGN PATENT DOCUMENTS

| | | | |
|---|---|---|---|
| 142317 | 5/1985 | European Pat. Off. | 423/328 |
| 2202838 | 10/1988 | United Kingdom | 423/328 |

Primary Examiner—R. Bruce Breneman
Attorney, Agent, or Firm—Cushman, Darby & Cushman

[57] ABSTRACT

A zeolite, designated zeolite NU-86, having a molar composition expressed by the formula 100 $XO_2$: equal to or less than 10 $Y_2O_3$: equal to less than 20 $R_{2/n}O$ where R is one or more cations of valency n, X is silicon and/or germanium, Y is one or more of aluminum, iron, gallium, boron, titanium, vanadium, zirconium, molybdenum, arsenic, antimony, chromium and manganese and having an X-ray diffraction pattern including the lines shown in Table 1 is prepared from a reaction mixture comprising $XO_2$ (preferably silica), $Y_2O_3$ (preferably alumina) and a polymethylene alpha, omega-diammonium cation. This zeolite is a useful catalyst for a variety of reactions.

18 Claims, 8 Drawing Sheets

ZEOLITES

The present invention relates to a novel zeolite hereinafter referred to as zeolite NU-86, to a method of making it, and to processes using it as a catalyst.

According to the present invention we provide a zeolite, designated zeolite NU-86, having a chemical composition expressed on an anhydrous basis, in terms of the mole ratios of oxides, by the formula: $100XO_2$: equal to or less than $10Y_2O_3$: equal to or less than $20R_{2/n}O$ where R is one or more cations of valency n, X is silicon and/or germanium, Y is one or more of aluminium, iron, gallium, boron, titanium, vanadium, zirconium, molybdenum, arsenic, antimony, chromium and manganese and having, in its as-prepared form, an X-ray diffraction pattern including the lines shown in Table 1.

The invention also provides zeolite NU-86 in its hydrogen form, designated H-NU-86, produced by calcination and/or ion-exchange as described herein. Zeolite H-NU-86 has an X-ray diffraction pattern including the lines shown in Table 2.

TABLE 1

| Zeolite NU-86 as-prepared | |
|---|---|
| d(Angstroms) | Relative Intensity(*) |
| 11.80 +/− 0.15 | w-m ⎫ |
| 11.10 +/− 0.15 | w-m ⎬ (a) |
| 10.65 +/− 0.15 | w   ⎭ |
| 8.60 +/− 0.15 | w |
| 4.22 +/− 0.10 | m |
| 4.15 +/− 0.10 | m   ⎫ (**) |
| 4.10 +/− 0.10 | w-m ⎭ |
| 3.94 +/− 0.08 | vs |
| 3.88 +/− 0.08 | s-vs |
| 3.74 +/− 0.07 | m |
| 3.45 +/− 0.06 | w |
| 3.35 +/− 0.06 | w |
| 3.11 +/− 0.06 | w |
| 2.07 +/− 0.04 | w |

(*)Based on a relative intensity scale in which the strongest line in the X-ray pattern is assigned a value of 100.
weak (w) is less than 20
medium (m) is between 20 and 40
strong (s) is greater than 40 but less than 60
very strong (vs) is greater than 60
(**)These lines occure as a doublet. However, in the diffractograms from which X-ray data are obtained the doublet may not be resolved and the lines may, therefore, appear as a single unresolved peak.

It has to be noted, and as will be appreciated by those skilled in the art, the data given in Table 1 is data obtained from relatively pure highly crystalline sample of material. When zeolite NU-86 is relatively pure and highly crystalline feature (a) as identified in Table 1 applies:- (a) denotes that this is a broad asymmetric reflection containing a number of peaks, the major ones of which are those occurring at d-spacings of 11.80, 11.10 and 10.65 Angstroms.

TABLE 2

| Zeolite NU-86 in its Hydrogen Form, H-NU-86 | |
|---|---|
| d(Angstroms) | Relative Intensity(*) |
| 11.80 +/− 0.15 | m   ⎫ |
| 11.10 +/− 0.15 | w-m ⎬ (a) |
| 10.60 +/− 0.15 | w-m ⎭ |
| 8.60 +/− 0.15 | w |
| 4.24 +/− 0.10 | w-m |
| 4.16 +/− 0.10 | w-m ⎫ (**) |
| 4.10 +/− 0.10 | w-m ⎭ |
| 3.93 +/− 0.08 | vs |
| 3.85 +/− 0.08 | s-vs |
| 3.73 +/− 0.08 | m |
| 3.54 +/− 0.06 | w |
| 3.10 +/− 0.06 | w |
| 2.07 +/− 0.04 | w |

(*), (**) and (a) are as hereinbefore defined

The diffractograms from which X-ray data were obtained (d-spacings and relative intensities) are characterised by broad reflections with many of the peaks occurring as shoulders on other more intense peaks. Some, or all, of the shoulders may not be resolved. This may occur for poorly crystalline samples or in samples in which the crystals are sufficiently small to result in significant X-ray broadening. It may also occur if the equipment, or conditions, used to obtain the pattern differ from those used herein.

The X-ray powder diffraction data provided herein were obtained with a Philips APD 1700 automated X-ray diffraction system using Cu K-alpha radiation from a long fine focus X-ray tube operating at 40 KV and 50 mA. The radiation was monochromatised by a curved graphite crystal adjacent to the detector. An automatic theta-compensating divergence slit was used with a 0.1 mm receiving slit. Step scanned data were collected between 1 and 60 degrees two-theta. The collected data were analysed in a DEC (Digital Equipment Corporation) Micro PDP -11/73 computer with Philips PW 1867/87 version 3.0 software. The X-ray computer intensities given herein are based on peak height.

It is believed that NU-86 has a new framework structure or topology which is characterised by its X-ray diffraction pattern. NU-86 in its "as-prepared" form has substantially the X-ray data given in Table 1 and is thereby distinguished from known zeolites.

Within the above definition of chemical composition the number of moles of $Y_2O_3$ per 100 moles of $XO_2$ is typically in the range 0.1 to 10 for example 0.2 to 7.5 and zeolite NU-86 appears to be most readily formed in a state of high purity when the number of moles of $Y_2O_3$ per 100 moles of $XO_2$ is in the range 0.4 to 6.

This definition includes "as-prepared" NU-86 and also forms of it resulting from dehydration and/or calcination and/or ion exchange. The expression "as-prepared" means the product of synthesis and washing with or without drying or dehydration. In its "as-prepared" form NU-86 may include M, an alkali-metal cation, especially sodium and/or ammonium and, when prepared for example from alkylated nitrogen compounds, may include nitrogen-containing organic cations as described below or degradation products thereof or precursors thereof. Such nitrogen-containing organic cations are hereinafter referred to as Q.

Thus zeolite NU-86, "as prepared", has the following molar composition, expressed on an anhydrous basis: 100 $XO_2$: less than or equal to 10 $Y_2O_3$: less than or equal to 10 Q: less than or equal to 10 $M_2O$ where Q is the nitrogen-containing organic cation referred to above and M is the alkali metal and/or ammonium cation.

The compositions for NU-86 above are given on an anhydrous basis, although "as-prepared" NU-86 and activated forms of NU-86 resulting from calcination and/or ion exchange may contain water. The molar $H_2O$ content of such forms, including "as-prepared" NU-86, depends on the conditions under which it has been dried and stored after synthesis or activation. The range of molar quantities of contained water is typically between 0 and 100 per 100 $XO_2$.

Calcined forms of zeolite NU-86 include no nitrogen-containing organic compound, or less than the "as-prepared" form, since the organic material is removed, usually by a thermal treatment such as burning the organic material out in the presence of air, leaving hydrogen ion as the other cation.

Among the ion-exchanged forms of zeolite NU-86 the ammonium ($NH_4^+$) form is of importance since it can be readily converted to the hydrogen form by calcination. The hydrogen form and forms containing metals introduced by ion exchange are described below. Under some circumstances exposure of the zeolite of the invention to acid can result in partial or complete removal of a framework element such as aluminium as well as the generation of the hydrogen form. This can provide a means of altering the composition of the zeolite material after it has been synthesised.

The invention also provides a method for the preparation of zeolite NU-86 which comprises reacting an aqueous mixture comprising a source of at least one oxide $XO_2$, a source of at least one oxide $Y_2O_3$, optionally a source of at least one oxide $M_2O$ and at least one nitrogen-containing organic cation Q, or precursors thereof, the mixture preferably having the molar composition:

$XO_2/Y_2O_3$ at least 10, more preferably 10 to 60, most preferably 15 to 50

$(R_{1/n})OH/XO_2$ is 0.01 to 2, more preferably 0.05 to 1, most preferably 0.10 to 0.75

$H_2O/XO_2$ is 1 to 500, more preferably 5 to 250, most preferably 25 to 75

$Q/XO_2$ is 0.005 to 1, more preferably 0.02 to 1, most preferably 0.05 to 0.5

$L_pZ/XO_2$ is 0 to 5, more preferably 0 to 1, most preferably 0 to 0.25 where X is silicon and/or germanium, Y is one or more of aluminium, iron, boron, titanium, vanadium, zirconium, molybdenum, arsenic, antimony, gallium, chromium, manganese, R is a cation of valency n which can include M, (an alkali metal cation and/or ammonium), and/or Q, (a nitrogen-containing organic cation, or a precursor thereof). In some circumstances it may be an advantage to add a salt $L_pZ$ where Z is an anion of valency p and L is an alkali metal or ammonium ion which may be the same as M or a mixture of M and another alkali metal or an ammonium ion necessary to balance the anion Z. Z may comprise an acid radical added for example as a salt of L or as a salt of aluminium. Examples of Z may include strong acid radicals such as bromide, chloride, iodide, sulphate, phosphate or nitrate or weak acid radicals such as organic acid radicals, for example citrate or acetate. While $L_pZ$ is not essential, it may accelerate the crystallisation of zeolite NU-86 from the reaction mixture and may also affect the crystal size and shape of NU-86. The reaction is continued until crystallisation has occurred.

Many zeolites have been prepared using nitrogen-containing organic cations or degradation products thereof or precursors thereof and in particular, polymethylene alpha omega-diammonium cations having the formula:

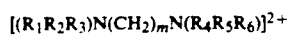

where $R_1$ to $R_6$, which may be the same or different, can be hydrogen, alkyl or hydroxyalkyl groups containing from 1 to 8 carbon atoms, and up to five of the groups can be hydrogen, and m is in the range 3 to 14. For example zeolite EU-1 (EP 42226), zeolite EU-2 (GB 2 077 709) and zeolite ZSM-23 (EP 125 078, GB 2 202 838) have been prepared using such templates.

Zeolite ZSM-23 may be prepared using such a template where m is 8. It has been found that zeolite NU-86 can also be prepared using this template but from reaction mixtures which contain higher proportions of alumina than those required for making ZSM-23 and, in particular, from a reaction mixture in which the $SiO_2/Al_2O_3$ molar ratios is less than 60.

In the method according to the present invention Q is such a polymethylene alpha, omega-diammonium cation, or an amine degradation product thereof, or a precursor thereof, in which m is 8 or 9.

M and/or Q can be added as hydroxides or salts of inorganic acids provided the $(R_{1/n})OH/XO_2$ ratio is fulfilled.

Suitable precursors of the nitrogen-containing organic cation Q include the parent diamine with a suitable alkyl halide or alkanol or the parent dihaloalkane with a suitable trialkylamine. Such materials can be used as simple mixtures or they can be pre-heated together in the reaction vessel, preferably in solution, prior to the addition of the other reactants required for the synthesis of zeolite NU-86.

The preferred cation M is an alkali metal especially sodium, the preferred $XO_2$ is silica ($SiO_2$) and the preferred oxide $Y_2O_3$ is alumina ($Al_2O_3$).

The silica source can be any of those commonly considered for use in synthesising zeolites, for example powdered solid silica, silicic acid, colloidal silica or dissolved silica. Among the powdered silicas usable are precipitated silicas, especially those made by precipitation from an alkali metal silicate solution, such as the type known as "KS 300" made by AKZO, and similar products, aerosil silicas, fumed silicas e.g. "CAB-O-SIL" and silica gels suitably in grades for use in reinforcing pigments for rubber and silicone rubber. Colloidal silicas of various particle sizes may be used, for example 10-15 or 40-50 microns, as sold under the Registered Trade Marks "LUDOX", "NALCOAG" and "SYTON". The usable dissolved silicas include commercially available waterglass silicates containing 0.5 to 6.0, especially 2.0 to 4.0 mols of $SiO_2$ per mol of alkali metal oxide, "active" alkali metal silicates as defined in UK Patent 1193254, and silicates made by dissolving silica in alkali metal hydroxide or quaternary ammonium hydroxide or a mixture thereof.

The optional alumina source is most conveniently sodium aluminate, or aluminium, an aluminium salt, for example the chloride, nitrate or sulphate, an aluminium alkoxide or alumina itself, which should preferably be in a hydrated or hydratable form such as colloidal alumina, pseudoboehmite, boehmite, gamma alumina or the alpha or beta trihydrate. Mixtures of the above can be used.

Optionally all or some of the alumina and silica source may be added in the form of an aluminosilicate.

The reaction mixture is usually reacted under autogenous pressure, optionally with added gas, e.g. nitrogen, at a temperature between 85° C. and 200° C., preferably between 120° C. and 180° C., and, most preferably, not more than 165° C. until crystals of zeolite NU-86 form, which can be from 1 hour to many months depending on the reactant composition and the operating temperature. Agitation is optional, but is preferable since it reduces the reaction time and can improve product purity.

The use of seed material can be advantageous in decreasing the time to nucleation and/or overall crystallisation time. It may also be an advantage in encouraging the formation of NU-86 at the expense of an impurity phase. Such seed materials include zeolites, especially crystals of zeolite NU-86. The seed crystals are usually added in an amount of between 0.01 and 10% of the weight of silica used in the reaction mixture.

At the end of the reaction, the solid phase is collected in a filter and washed, and is then ready for further steps such as drying, dehydration and ion exchange.

If the product of the reaction contains alkali metal ions, these have to be at least partly removed in order to prepare the hydrogen form of NU-86 and this can be done by ion-exchange with an acid, especially a mineral acid such as hydrochloric acid or by way of the ammonium compound, made by ion exchange with a solution of an ammonium salt such as ammonium chloride. Ion exchange may be carried out by slurrying once or several times with the ion exchange solution. The zeolite is usually calcined before ion exchange to remove any occluded organic matter since this usually facilitates ion exchange.

In general, the cation(s) of zeolite NU-86 can be replaced by any cation(s) of metals, and particularly those in groups 1A, 1B, IIA, IIB, IIIA, IIIB (including rare earths) and VIII (including noble metals) of the Periodic Table, other transition metals and by tin, lead and bismuth. (The Periodic Table is as in "Abridgements of Specifications" published by the UK Patent Office). Exchange is normally carried out using a solution containing a salt of the appropriate cation.

The invention also provides a catalyst composition comprising zeolite NU-86 and catalytic processes employing zeolite NU-86 as the catalyst.

In the catalysts according to the invention $XO_2$ is preferably silica and $Y_2O_3$ is preferably alumina. Such catalysts may be used in a wide variety of catalytic processes and using a wide variety of feedstocks.

Catalytically useful forms of zeolite NU-86 include the hydrogen and ammonium forms, prepared by the methods hereinbefore described.

Catalysts according to the invention comprising NU-86 may also comprise one or more elements, especially metals or cations thereof, or compounds of said elements, especially metal oxides. Such catalysts may be prepared by ion-exchange or impregnation of zeolite NU-86 with the said element, cation or compound, or a suitable precursor of said cation or compound. Such ion-exchange or impregnation may be carried out on the "as-prepared" zeolite NU-86, the calcined form, the hydrogen form and/or the ammonium form and/or any other exchanged form.

In cases where a metal-containing form of zeolite NU-86 is prepared by ion-exchange it may be desirable to effect complete exchange of the metal, by which is meant that substantially all of the exchangeable sites are occupied by the metal. Such forms may be particularily useful in separation processes. In most cases, however, it is preferable to effect only partial exchange of the metal, the remaining sites being occupied by another cation especially hydrogen or ammonium cations. In some cases it may be desirable to introduce two or more metal cations by ion exchange.

In cases where zeolite NU-86 is impregnated with a metal compound to form a catalyst, the metal compound may be added in any suitable quantity, but 20% by weight is generally sufficient for most applications; for some applications up to 10% by weight is sufficient, and quantities of up to 5% are often appropriate. Impregnation may be carried by any suitable method known in the art of catalyst preparation.

Metal-exchanged forms or forms in which a metal compound has been impregnated may be used as such or they may be treated to produce an active derivative. Treatments include reduction, for example in an atmosphere comprising hydrogen, to produce a metal or other reduced forms. Such treatments may be carried out at a suitable stage in the catalyst preparation or may conveniently be carried out in the catalytic reactor.

Catalytic compositions comprising zeolite NU-86 can, if desired, be associated with an inorganic matrix which may be either inert or catalytically active. The matrix may be present solely as a binding agent to hold the zeolite particles together, possibly in a particular shape or form, for example as a pellet or extrudate, or it may function as an inert diluent, for example to control the activity per unit weight of catalyst. When the inorganic matrix or diluent is itself catalytically active it can thereby form an effective part of the zeolite/matrix catalyst composition. Suitable inorganic matrices and diluents include conventional catalyst support materials such as silica, the various forms of alumina, clays such as bentonites, montmorillonites, sepiolite, attapulgite, Fullers Earth and synthetic porous materials such as silica-alumina, silica-zirconia, silica-thoria, silica-beryllia or silica-titania. Combinations of matrices are contemplated within the present invention, especially combinations of inert and catalytically-active matrices.

When zeolite NU-86 is associated with an inorganic matrix material or a plurality thereof, the proportion of matrix material or materials in the total composition usually amounts to up to about 90% by weight, preferably up to 50% by weight, more preferably up to 30% by weight.

For some applications another zeolite or molecular sieve may be used in conjunction with zeolite NU-86 to form a catalyst. Such a combination may be used as such or associated with one or more matrix materials hereinbefore described. A particular example of the use of such an overall composition is as a fluid catalytic cracking catalyst additive, in which case zeolite NU-86 is preferably used in an amount of 0.5 to 5% by weight of the total catalyst.

For other applications zeolite NU-86 may be combined with another catalyst, such as platinum on alumina.

Any convenient method of mixing zeolite NU-86 with an inorganic matrix and/or another zeolite material, may be employed, especially that suited to the final form in which the catalyst is used, for example extrudates, pellets or granules.

If zeolite NU-86 is used to form a catalyst in conjunction with a metal component (for example, a hydrogenation/dehydrogenation component or other catalytically active metal) in addition to an inorganic matrix, the metal component can be exchanged or impregnated into the zeolite NU-86 itself before addition of the matrix material or into the zeolite-matrix composition. For some applications it may be advantageous to add the metal component to the whole or part of the matrix material before mixing the latter with the zeolite NU-86.

A wide range of hydrocarbon conversion catalysts comprising zeolite NU-86 can be prepared by ion-exchange or impregnation of the zeolite with one or more cations or oxides derived from elements selected from Cu, Ag, Ga, Mg, Ca, Sr, Zn, Cd, B, Al, Sn, Pb, V, P, Sb, Cr, Mo, W, Mn, Re, Fe, Co, Ni and noble metals.

In cases where catalysts comprising zeolite NU-86 contain one or more hydrogenation/dehydrogenation components such as the metals Ni, Co, Pt, Pd, Re and Rh, such components can be introduced by ion-exchange or impregnation of a suitable compound of the metal.

Catalyst compositions comprising zeolite NU-86 may find application in reactions involving saturated and unsaturated aliphatic hydrocarbons, aromatic hydrocarbons, oxygenated organic compounds and organic compounds containing nitrogen and/or sulphur as well as organic compounds containing other functional groups.

In general, catalyst compositions comprising zeolite NU-86 can be usefully employed in reactions involving isomerisation, transalkylation and disproportionation, alkylation and de-alkylation, dehydration and hydration, oligomerisation and polymerisation, cyclisation, aromatisation, cracking, hydrogenation and dehydrogenation, oxidation, halogenation, synthesis of amines, hydrodesulphurisation and hydrodenitrification, ether formation and synthesis of organic compounds in general.

The above processes may be carried out in either the liquid or vapour phase under conditions which are chosen as suitable for each individual reaction. For example, the reactions carried out in the vapour phase may involve the use of fluid bed, fixed bed or moving bed operations. Process diluents may be used when required. Depending upon the particular process, suitable diluents include inert gases (such as nitrogen or helium), hydrocarbons, carbon dioxide, water or hydrogen. The diluent may be inert or it may exert a chemical effect. It may be an advantage, especially in cases where hydrogen is used, to include a metal component, such as a hydrogenation/dehydrogenation component, for example one or more of the metals, Ni, Co, Pt, Pd, Re or Rh as part of the catalyst composition.

According to a further aspect of the present invention we provide a hydrocarbon conversion process which comprises contacting an alkylbenzene or a mixture of alkylbenzenes under isomerisation conditions in the vapour or liquid phase with a catalyst comprising zeolite Nu-86.

Isomerisation reactions for which catalysts comprising zeolite NU-86 are of particular use are those involving alkanes and substituted aromatic molecules, especially xylenes. Such reactions may include those which can be carried out in the presence of hydrogen. Catalyst compositions containing zeolite NU-86 which are of particular use in isomerisation reactions include those in which the NU-86 is in its acid (H) form, cation-exchanged form, or other metal-containing forms or combinations thereof. Especially useful are those forms in which the metal is a hydrogenation/dehydrogenation component such as Ni, Co, Pt, Pd, Re or Rh.

Particular isomerisation reactions in which a catalyst comprising NU-86 may be found useful include xylene isomerisation and hydroisomerisation of xylenes, paraffin, in particular $C_4$ to $C_{10}$ normal hydrocarbons, or olefin isomerisation and catalytic dewaxing.

Xylene isomerisation and hydroisomerisation may be carried out in the liquid or vapour phase. In the liquid phase, suitable isomerisation conditions include a temperature in the range 0°-350° C., a pressure in the range 1-200 atmospheres absolute, preferably 5-70 atmospheres absolute, and when conducted in a flow system, a weight hourly space velocity (WHSV) preferably in the range 1-30 hr$^{-1}$ based on the total catalyst composition. Optionally, a diluent may be present, suitably one or more of those having a critical temperature higher than the isomerisation conditions being used. The diluent, if present, may comprise 1-90% by weight of the feed. Vapour phase xylene isomerisation and hydroisomerisation reactions are most suitably carried out at a temperature in the range 100°-600° C., preferably 200°-500° C., at a pressure in the range 0.5-100 atmosphere absolute, preferably 1-50 atmospheres absolute, and at a WHSV up to 80 based on the total catalyst composition.

When xylene isomerisation is conducted in the presence of hydrogen (in the vapour phase), the preferred hydrogenation/dehydrogenation component is Pt or Ni. The hydrogenation/dehydrogenation component is usually added in an amount of between 0.05 and 2% by weight of the total catalyst. Additional metals and/or metal oxides may be present in the catalyst composition.

In xylene isomerisation, ethylbenzene may be present in the xylene feed in amounts up to 40% by weight. Over catalyst compositions comprising zeolite NU-86 the ethylbenzene will undergo transalkylation with itself, and with xylenes, to form heavier and lighter aromatic compounds. The ethylbenzene will also react to form benzene and light gas, particularly at temperatures above 400° C. With such xylene feeds containing ethylbenzene, when reaction is carried out in the presence of hydrogen over a catalyst composition comprising zeolite NU-86 together with a hydrogenation/dehydrogenation component, some of the ethylbenzene will isomerise to xylenes. It may also be an advantage to carry out xylene isomerisation reactions in the presence of a hydrocarbon compound, especially a paraffin or naphthene with or without the additional presence of hydrogen. The hydrocarbon appears to improve catalyst performance in that reactions which lead to xylenes loss are suppressed and, particularly when reactions are carried out in the absence of hydrogen, catalyst life is extended.

According to yet a further aspect of the present invention we provide a hydrocarbon conversion process which comprises contacting one or more alkylated aromatic compounds under transalkylation conditions in the vapour or liquid phase with a catalyst comprising zeolite NU-86.

Catalysts comprising zeolite NU-86 are of special value in transalkylation and disproportionation reactions, in particular those reactions involving mono-, di-, tri- and tetra-alkyl substituted aromatic molecules, especially toluene and xylenes.

Catalyst compositions comprising NU-86 which are of particular use in transalkylation and disproportionation reaction include those in which the NU-86 component is in its acid (H) form, its cation-exchanged form, or other metal-containing forms or combinations thereof. Especially useful is the acid form and those forms in which the metal is a hydrogenation/dehydrogenation component such as Ni, Co, Pt, Pd, Re or Rh.

Particular examples of important processes include toluene disproportionation and the reaction of toluene with aromatic compounds containing 9 carbon atoms, for example trimethyl benzenes.

Toluene disproportionation can be conducted in the vapour phase either in the presence or absence of hydrogen, although the presence of hydrogen is preferred as this helps to suppress catalyst deactivation. The most suitable reaction conditions are: temperatures in the range 250°–650° C., preferably 300°–550° C.; pressures in the range 0.3–100 atmospheres absolute, preferably 1–50 atmospheres absolute; weight hourly space velocity up to 50 (based on the total catalyst composition).

When toluene disproportionation is conducted in the presence of hydrogen the catalyst may, optionally, contain a hydrogenation/dehydrogenation component. The preferred hydrogenation/dehydrogenation component is Pt, Pd, or Ni. The hydrogenation/dehydrogenation component is normally added in a concentration of up to 5% by weight of the total catalyst composition. Additional metals and/or metal oxides may be present in the catalyst composition, for example up to 5% by weight of the total catalyst, composition.

The present invention further provides a hydrocarbon conversion process which comprises reacting an olefinic or aromatic compound with a suitable alkylating compound under alkylating conditions in the vapour or liquid phase over a catalyst comprising zeolite NU-86.

Among the alkylation reactions for which catalysts comprising zeolite NU-86 are of particular use are the alkylation of benzene or substituted aromatic molecules with methanol or an olefin or ether. Specific examples of such processes include toluene methylation, ethylbenzene synthesis, and the formation of ethyl toluene and cumene. Alkylation catalysts used in processes according to this further aspect of the invention may comprise further materials, especially metal oxides which may improve catalytic performance.

Catalysts comprising zeolite NU-86 may find application in reactions involving the dehydration of alcohols, for example methanol and higher alcohols, to form hydrocarbons, including olefins and gasoline. Other feedstocks for dehydration reactions involving a catalyst comprising NU-86 include ethers, aldehydes and ketones.

By the use of a catalyst comprising NU-86, hydrocarbons can be generated by carrying out oligomerisation, cyclisation and/or aromatisation reactions on unsaturated compounds such as ethene, propene or butene, on saturated compounds such as propane or butane or mixtures of hydrocarbons such as light napthas. For some reactions, particularly aromatisation reactions, the catalyst may usefully comprise a metal or metal oxide, especially platinum, gallium, zinc or their oxides.

Catalysts comprising NU-86 are of use in a variety of cracking reactions, including the cracking of olefins, paraffins or aromatics or mixtures thereof. Of particular value is the use of zeolite NU-86 as a fluid catalytic cracking catalyst additive to improve the product of the cracking reaction. Zeolite NU-86 may also be used as a component of a catalyst in catalytic dewaxing or hydrocracking processes.

Hydrogenation/dehydrogenation processes, for example the dehydrogenation of alkanes to the corresponding olefins, are suitably carried out by contacting the appropriate feedstock under appropriate conditions with a catalyst comprising zeolite NU-86, especially when the latter also comprises a hydrogenation/dehydrogenation component such as Ni, Co, Pt, Pd, Re or Ru.

Zeolite NU-86 is useful as a component in a catalyst for the preparation of amines, for example the production of methylamines from methanol and ammonia.

Zeolite NU-86 is also a useful catalyst for the formation of ethers, particularly by the reaction of two alcohols or by the reaction of an olefin with an alcohol.

The invention is illustrated by the following non-limiting examples.

EXAMPLE 1

A reaction mixture of molar composition:

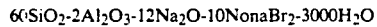

$60SiO_2 \cdot 2Al_2O_3 \cdot 12Na_2O \cdot 10NonaBr_2 \cdot 3000H_2O$ was prepared from:
- 51.5 g "CAB-O-SIL" (BDH Ltd)
- 8.114 g Sodium Aluminate (BDH Ltd: 27.5% w/w Na$_2$O, 35.9% w/w Al$_2$O$_3$ 36.6% w/w H$_2$O)
- 10.83 g Sodium Hydroxide
- 135.3 g NonaBr$_2$ solution (containing 42.7% w/w NonaBr$_2$ in water)
- 689.2 g Water where NonaBr$_2$ is Nonamethonium Bromide:

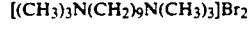

$[(CH_3)_3N(CH_2)_9N(CH_3)_3]Br_2$

The mixture was prepared as follows:
- A—dispersion of the CAB-O-SIL in about 345 g of water
- B—solution containing sodium aluminate and sodium hydroxide in the remaining water
- C—NonaBr$_2$ solution Solution B was added to solution C and the mixture added, with stirring, to dispersion A. Stirring was continued until a smooth gel was obtained. The resulting mixture was transferred to a 1 liter stainless steel autoclave.

The mixture was reacted at 160° C. with stirring at 300 rpm using a pitched-paddle type impeller. Samples were withdrawn from the reactor periodically and examined for evidence of crystallisation. After 650 hours at reaction temperature the preparation was crash cooled to ambient temperature and the product discharged. The product was filtered, washed with demineralised water and dried at 110° C.

Figure 1:
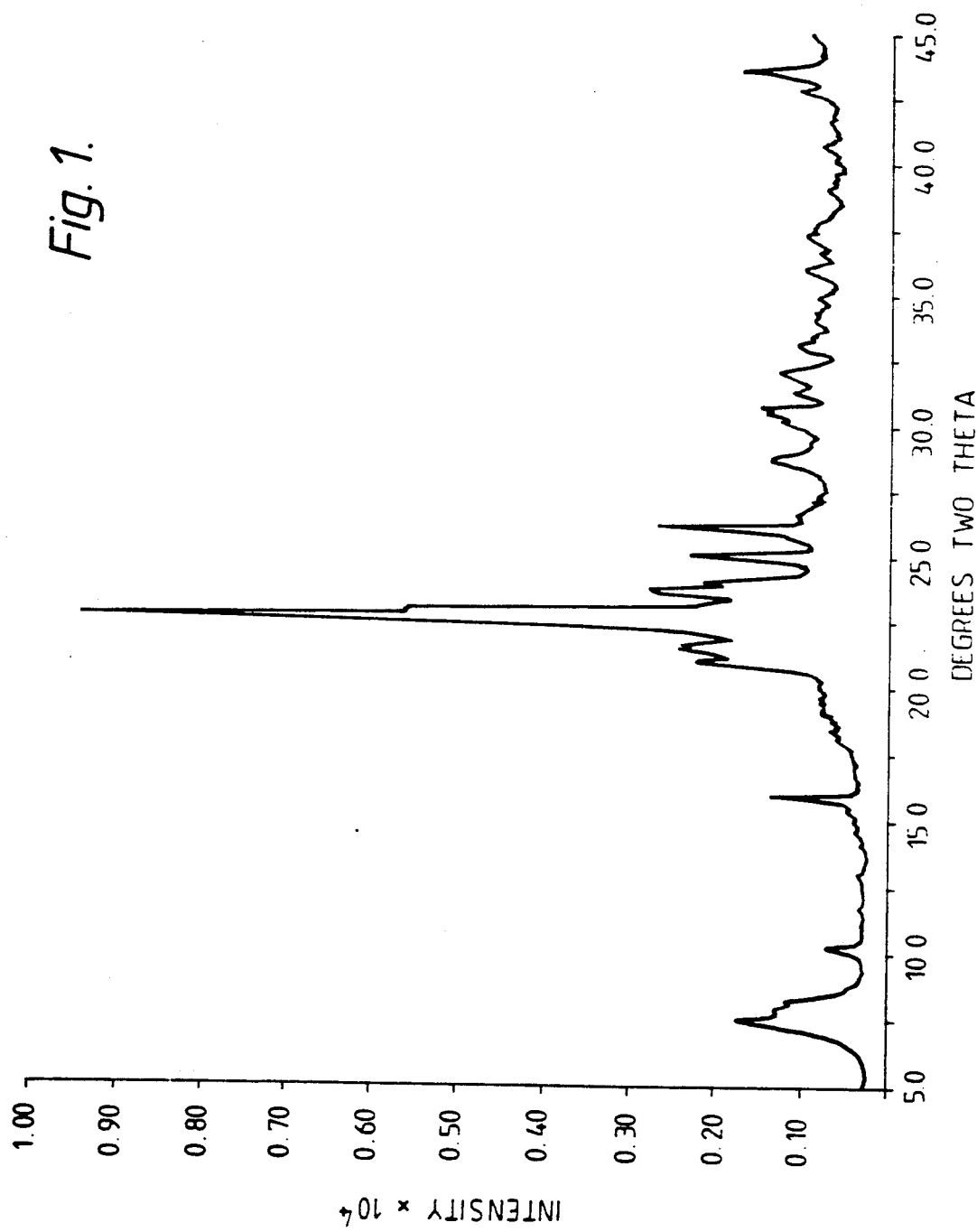
FIG. 1 is the X-ray diffraction pattern of the product of Example 1.

The product was analysed by X-ray powder diffraction and found to be zeolite NU-86 together with a small amount, less than 10%, of analcime. The diffraction pattern is given in FIG. 1 and the interplanar spacings and intensities in Table 3.

EXAMPLE 2

A reaction mixture of molar composition:

$60SiO_2\text{-}1.714Al_2O_3\text{-}9Na_2O\text{-}10NonaBr_2\text{-}3000H_2O$ was prepared from:
- 42.2 g "CAB-O-SIL" (BDH Ltd)
- 5.34 g Sodium Aluminate (BDH Ltd: molar composition $1.2Na_2O\text{-}Al_2O_3\text{-}4.92H_2O$)
- 6.54 g Sodium Hydroxide
- 111.4 g NonBr$_2$ solution (containing 42.7% w/w NonaBr$_2$ in water)
- 568.7 g Water The mixture was prepared as follows:
- A—dispersion of the CAB-O-SIL in about half of the total water
- B—solution containing sodium aluminate and sodium hydroxide in the remaining water
- C—NonaBr$_2$ solution Solution B was added to solution C and the mixture added, with stirring, to dispersion A. Stirring was continued until a smooth gel was obtained. The resulting mixture was transferred to a 1 liter stainless steel autoclave.

The mixture was reacted at 160° C. Due to a fault, the reaction mixture was not stirred for an early part of the experiment. However, for the majority of the reaction time the mixture was stirred at 300 rpm using a pitched-paddle type impeller. Samples were withdrawn from the reactor periodically and examined for evidence of crystallisation. After 840 hours at reaction temperature the preparation was crash cooled to ambient temperature and the product discharged. The product was filtered, washed with demineralised water and dried at 110° C.

Figure 2:
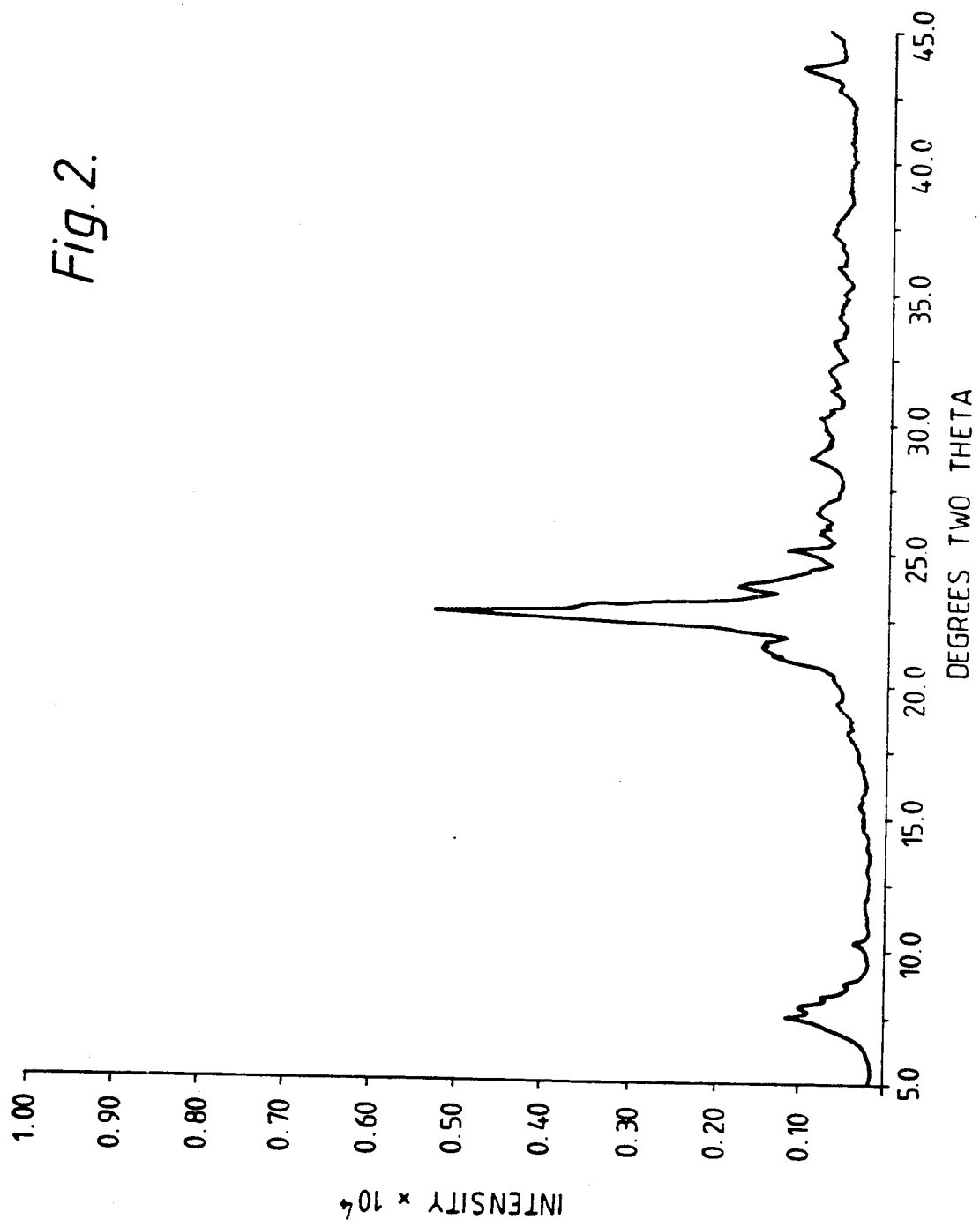
FIG. 2 is the X-ray diffraction pattern of the product of Example 2.

The product was analysed by X-ray powder diffraction and found to be zeolite NU-86 containing no detectable impurities. The diffraction pattern is given in FIG. 2 and the interplanar spacings and intensities in Table 4.

EXAMPLE 3: PREPARATION OF H-NU-86

A portion of the material from Example 1 was calcined, in air, as follows:
(a) 300° C. for 1 hour;
(b) 370° C. for 2 hours;
(c) 450° C. for 16 hours; and
(d) 500° C. for 24 hours.

The resulting material was then contacted for 2 hours, at room temperature, with a 1 molar solution of ammonium chloride, using 10 ml of solution per gram of zeolite. The solid product was filtered, washed and dried and the ion-exchange procedure repeated. The material was then calcined, in air, at 550° C. for 16 hours. The ion-exchange was again repeated. The resulting NH$_4$-NU-86 was filtered, washed and dried. Finally the product was calcined, in air, at 550° C. for 16 hours.

Analysis for Si, Al and Na revealed the following molar composition:

$29.5SiO_2\text{-}Al_2O_3\text{-}0.04Na_2O$

EXAMPLE 4: PREPARATION OF H-NU-86

A portion of the material from Example 1 was calcined, in air, as follows:
(a) 300° C. for 1 hour;
(b) 370° C. for 2 hours;
(c) 450° C. for 16 hours; and
(d) 500° C. for 24 hours.

The resulting material was then contacted for 4 hours, at room temperature, with a 1 molar solution of ammonium chloride, using 10 ml of solution per gram of zeolite. The solid product was filtered, washed and dried and the ion-exchange procedure repeated. The resulting NH$_4$-NU-86 was filtered, washed and dried. Finally the material was calcined, in air, at 550° C. for 16 hours.

Analysis for Si, Al and Na revealed the following molar composition:

$25.0SiO_2\text{-}Al_2O_3\text{-}0.05Na_2O$

Analysis by powder X-ray diffraction showed the material to be H-NU-86. The XRD interplanar spacings and intensities are given in Table 5.

EXAMPLE 5: PREPARATION OF H-NU-86

A portion of the material from Example 2 was calcined, in air, as follows:
(a) 300° C. for 1 hour;
(b) 370° C. for 2 hours;
(c) 450° C. for 16 hours; and
(d) 500° C. for 24 hours.

The resulting material was then contacted for 2 hours, at room temperature, with a 1 molar solution of ammonium chloride, using 10 ml of solution per gram of zeolite. The solid product was filtered, washed and dried and the ion-exchange procedure repeated. The resulting NH$_4$-NU-86 was filtered, washed and dried. It was then calcined in air at 550° C. for 16 hours.

Analysis for Si, Al and Na revealed the following molar composition:

$31.5SiO_2\text{-}Al_2O_3\text{-}0.002Na_2O$

Analysis by powder X-ray diffraction showed the material to be H-NU-86. The XRD interplanar spacings and intensities are given in Table 6.

The sorptive capacity of this material for molecules of various sizes was measured. Table 7 contains the sorption results.

The data were obtained using a CI Robal Microbalance for all sorbates. Samples were calcined in air at 450° C. for 7 hours and then evacuated at the same temperature for at least 2 hours before measurements were made. Results are presented as w/w uptake at a relative pressure (P/P$_o$) of 0.5, where P$_o$ is the saturated vapour pressure. The figures for apparent voidage filled were calculated assuming that the liquids maintain their normal densities at the sorption temperature.

TABLE 7

| Sorption data for product of Example 5 | | | |
|---|---|---|---|
| Sorbate | Kinetic Diameter[1]/ nm | Uptake[2] % w/w | Apparent Voidage filled/cm$^3$g$^{-1}$ |
| n-heptane | 0.43 | 12.3 | 0.18 |
| cyclohexane | 0.60 | 13.2 | 0.17 |

TABLE 7-continued

| | Sorption data for product of Example 5 | | |
|---|---|---|---|
| Sorbate | Kinetic Diameter[1]/ nm | Uptake[2] % w/w | Apparent Voidage filled/cm$^3$g$^{-1}$ |
| m-xylene | 0.62 | 0.45 | 0.005 |

[1]Kinetic diameters are taken from "Zeolite Molecular Sieves". D W Breck, J Wiley and Sons, 1976 p636. The value for n-heptane was assumed to be the same as for n-butane.
[2]The uptake is grams of sorbate per 100 grams of anhydrous zeolite.

The results show that NU-86 has significant, and similar, capacity for n-heptane and cyclohexane. Furthermore, the results also show that NU-86 has a molecular sieving effect with respect to m-xylene since much a lower uptake was observed compared with the other sorbates. Indeed the figure is so low that it indicates m-xylene is effectively excluded from the structure because it of its size relative to the window size of the zeolite. This result suggests that zeolite NU-86 has a window size close to 0.62 nm, the diameter of m-xylene.

EXAMPLE 6: PREPARATION OF NU-86

A reaction mixture of molar composition $$60SiO_2 - 2.18Al_2O_3 - 12Na_2O - 10OctaBr_2 - 3000H_2O$$

was prepared from:
- 45.06 g "CAB-O-SIL" (BDH Ltd)
- 12.516 g Sodium Aluminate solution (22.2% w/w Al$_2$O$_3$, 21.5% w/w Na$_2$O, 56.3% w/w H$_2$O)
- 8.53 g Sodium Hydroxide
- 48.78 g OctaBr$_2$
- 666.6 g Water where OctaBr$_2$ is Octamethonium Bromide:

$$[(CH_3)_3N(CH_2)_8N(CH_3)_3]Br_2$$

The mixture was prepared as follows:
A—dispersion of the "CAB-O-SIL" in ⅓ of the water
B—solution containing sodium aluminate and sodium hydroxide in ⅓ of the water
C—solution containing OctaBr$_2$ in the remaining water Solution B was added to dispersion A with stirring. Solution C was then added with stirring. Stirring was continued for about 5 minutes until a homogenous gel was obtained. The resulting mixture was transferred to a 1 liter stainless steel autoclave.

The mixture was reacted at 165° C. with stirring at 300 rpm using a pitched-paddle type impeller. Samples were withdrawn from the reactor periodically and examined for evidence of crystallisation. Due to fault in the power supply, the reaction mixture cooled to about ambient temperature before being heated back up to reaction temperature on two occasions. After 556 hours at reaction temperature the preparation was crash cooled to ambient temperature and the product discharged. The product was filtered, washed with demineralised water and dried at 110° C.

Figure 3:
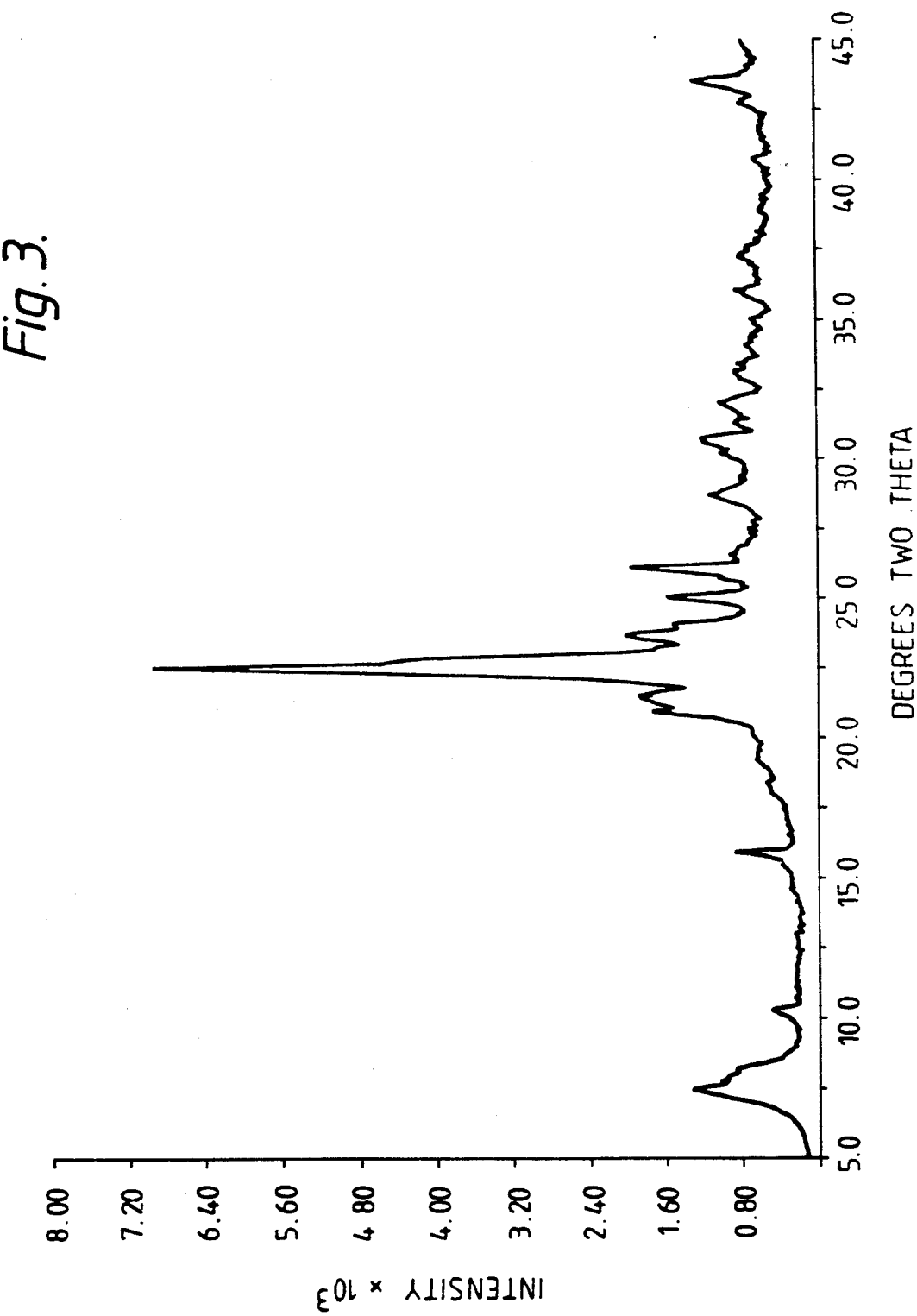
FIG. 3 is the X-ray diffraction pattern of the product of Example 6.

The product was analysed by X-ray powder diffraction and found to be a highly crystalline sample of NU-86 containing a small amount, about 5%, of analcime. The diffraction pattern is given in FIG. 3.

Analysis for Si, Al and Na revealed the following molar composition:

$$18.3SiO_2 - Al_2O_3 - 0.19Na_2O$$

EXAMPLE 7: PREPARATION OF H-NU-86

A portion of the material from Example 6 was heated under a flow of nitrogen gas for 24 hours at 450° C. followed by 16 hours at 550° C.

The resulting material was then contacted for 2 hours, at 60° C., with a 1 molar solution of ammonium chloride, using 10 ml of solution per gram of zeolite. The solid product was filtered, washed, dried at 110° C. and then the ion-exchange procedure repeated. The material was then calcined, in air, for 16 hours at 550° C. The ion-exchange was again repeated. The resulting NH$_4$-NU-86 was filtered, washed and dried. Finally the product was heated under a flow of nitrogen gas for 16 hours at 550° C.

Analysis for Si, Al and Na revealed the following molar composition:

$$20.4SiO_2 - Al_2O_3 - 0.02Na_2O$$

Figure 4:
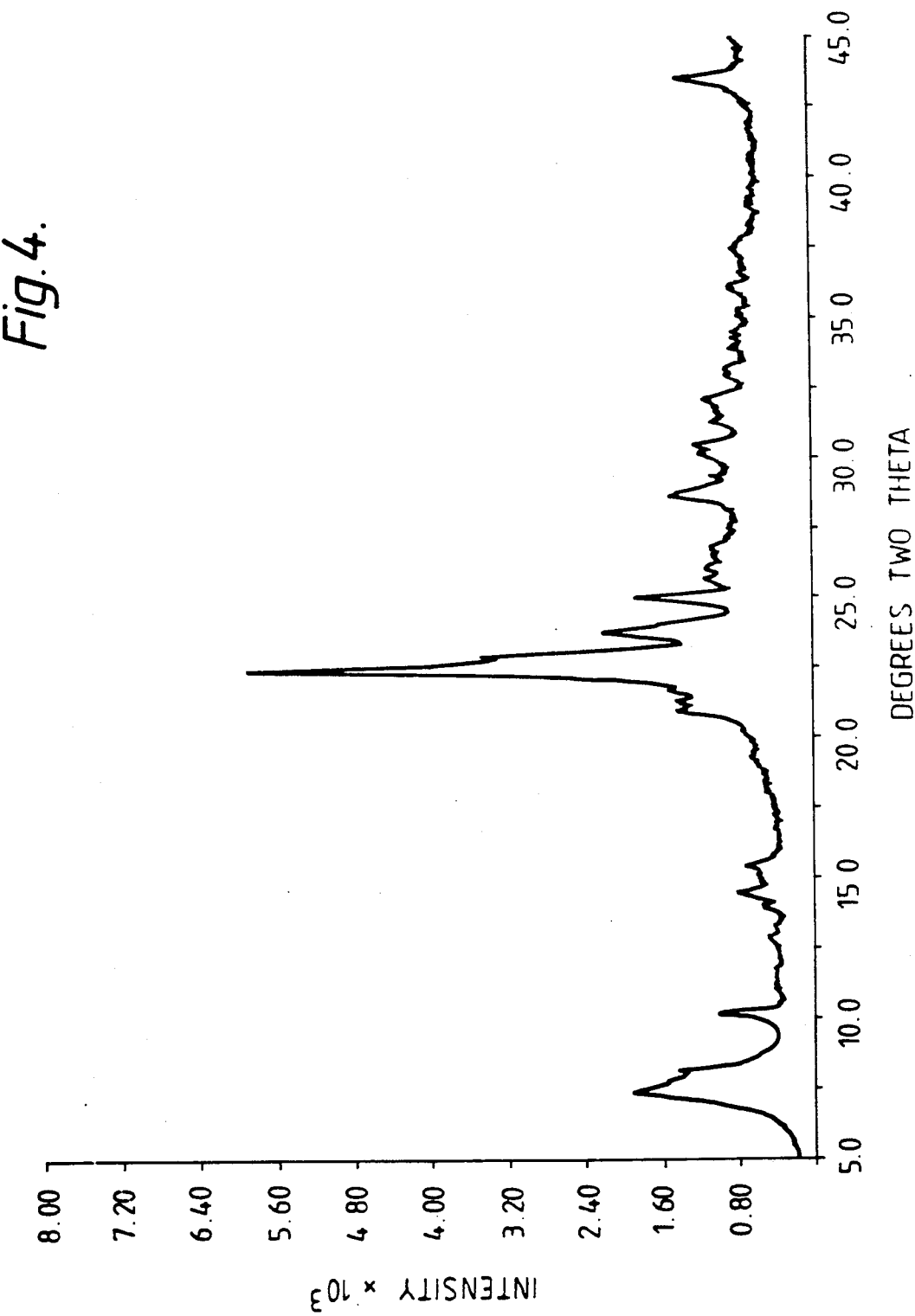
FIG. 4 is the X-ray diffraction pattern of the product of Example 7.

Examination of the material by X-ray powder diffraction showed it had a pattern consistent with it being H-NU-86. The diffraction pattern is given in FIG. 4 and the interplanar spacings and intensities in Table 8.

EXAMPLE 8: PREPARATION OF NU-86

A reaction mixture of molar composition $$60SiO_2 - 1.846Al_2O_3 - 12Na_2O - 15OctaBr_2 - 3000H_2O$$

was prepared from:
- 45.06 g "CAB-O-SIL" (BDH Ltd)
- 10.689 g Sodium Aluminate solution (22.01% w/w Al$_2$O$_3$, 19.81% w/w Na$_2$O, 58.18% w/w H$_2$O)
- 9.27 g Sodium Hydroxide
- 48.78 g OctaBr$_2$
- 667.27 g Water The mixture was prepared as follows:
A—dispersion of the "CAB-O-SIL" in ⅓ of the water
B—solution containing sodium aluminate and sodium hydroxide in ⅓ of the water
C—solution containing OctaBr$_2$ in the remaining water Solution B was added to dispersion A with stirring. Solution C was then added with stirring. Stirring was continued for about 5 minutes until a homogenous gel was obtained. The resulting mixture was transferred to a 1 liter stainless steel autoclave.

The mixture was reacted at 165° C. with stirring at 300 rpm using a pitched-paddle type impeller. Samples were withdrawn from the reactor periodically and examined for evidence of crystallisation.

After 550.5 hours at reaction temperature the preparation was crash cooled to ambient temperature and the product discharged. The product was filtered, washed with demineralised water and dried at 110° C.

Figure 5:
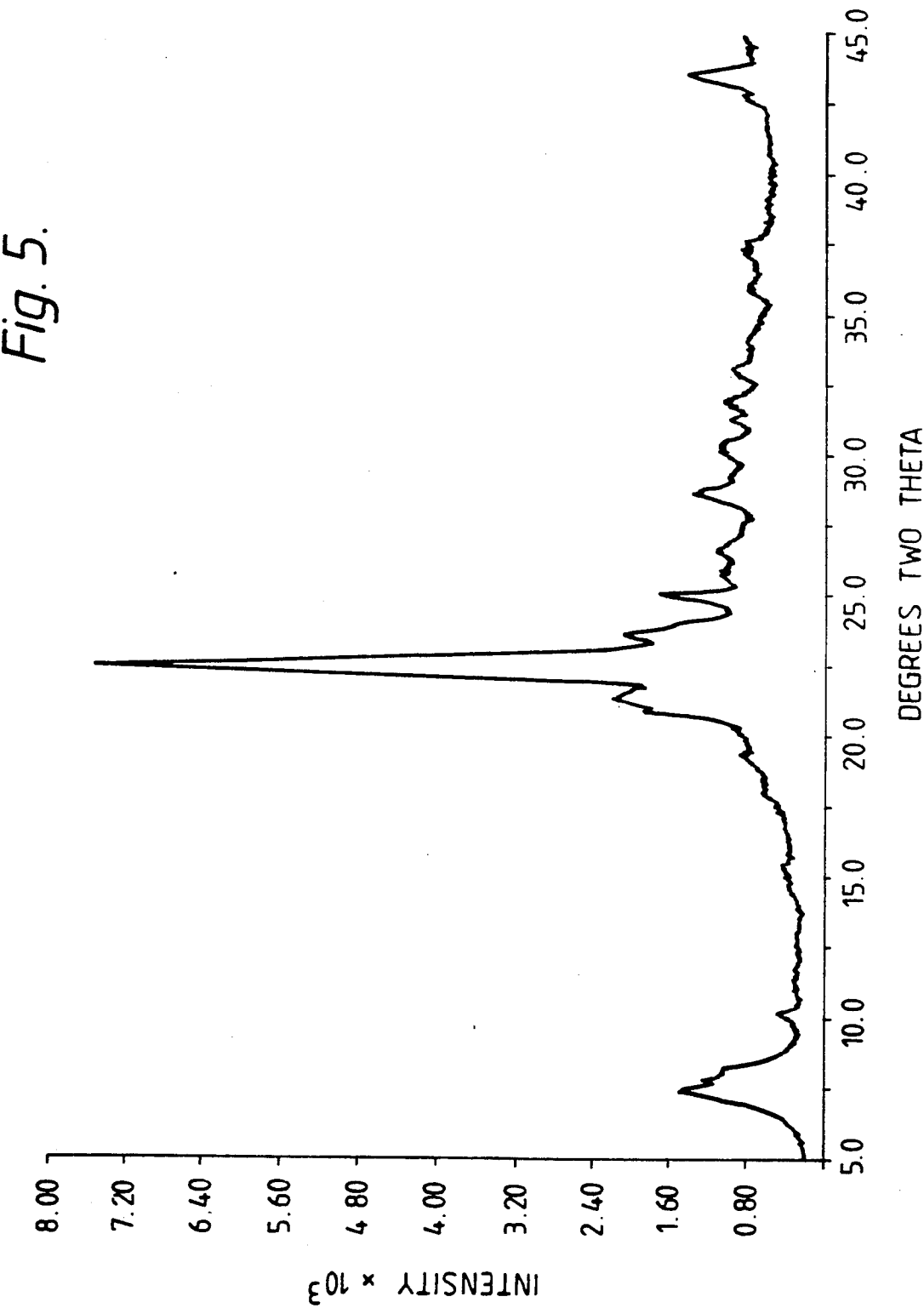
FIG. 5 is the X-ray diffraction pattern of the product of Example 8.

The product was analysed by X-ray powder diffraction and found to be a highly crystalline sample of NU-86. The diffraction pattern is given in FIG. 5.

Analysis for Si, Al and Na revealed the following molar composition:

$$19.4SiO_2 - Al_2O_3 - 0.008Na_2O$$

EXAMPLE 9: PREPARATION OF H-NU-86

A portion of the material from Example 8 was heated under a flow of nitrogen gas at 450° C. for 24 hours followed by 16 hours at 550° C.

The resulting material was then contacted for 2 hours, at 60° C., with a 1 molar solution of ammonium chloride, using 10 ml of solution per gram of zeolite. The solid product was filtered, washed, dried at 110° C. and then the ion-exchange procedure repeated. The material was then calcined, in air, for 16 hours at 550° C. The ion-exchange was again repeated. The resulting NH$_4$-NU-86 was filtered, washed and dried. Finally the product was heated under a flow of nitrogen gas for 16 hours at 550° C.

Analysis for Si, Al and Na revealed the following molar composition:

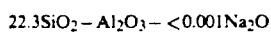

$22.3SiO_2 - Al_2O_3 - <0.001Na_2O$

Figure 6:
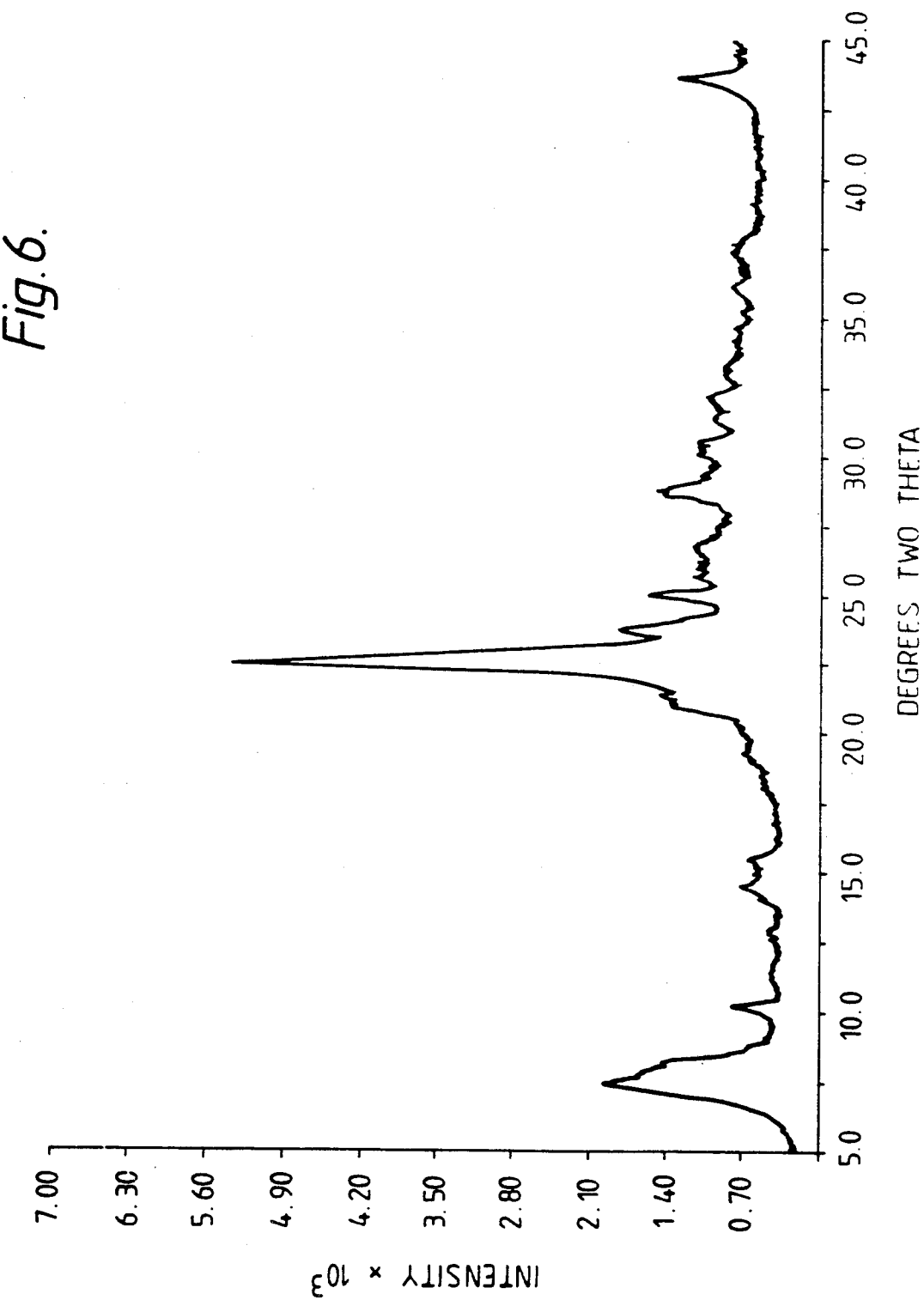
FIG. 6 is the X-ray diffraction pattern of the product of Example 9.

Examination of the material by X-ray powder diffraction showed it had a pattern consistent with it being H-NU-86. The diffraction pattern is given in FIG. 6 and the interplanar spacings and intensities in Table 9.

EXAMPLE 10: PREPARATION OF H-NU-86

A reaction mixture of molar composition

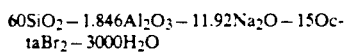

$60SiO_2 - 1.846Al_2O_3 - 11.92Na_2O - 15OctaBr_2 - 3000H_2O$ was prepared from:
45.1 g "CAB-O-SIL" (BDH Ltd)
10.42 g Sodium Aluminate solution (22.58% w/w Al$_2$O$_3$, 19.68% w/w Na$_2$O, 57.74% w/w H$_2$O)
9.27 g Sodium Hydroxide
73.2 g OctaBr$_2$ (solid)
667.5 g Water The mixture was prepared as follows:
A—dispersion of the "CAB-O-SIL" in about 220 g of the water
B—solution containing sodium aluminate and sodium hydroxide in about 220 g of the water
C—solution containing OctaBr$_2$ in the remaining water Solution B was added to dispersion A with stirring. Solution C was then added with stirring. Stirring was continued until a homogenous gel was obtained. The resulting mixture was transferred to a 1 liter stainless steel autoclave.

The mixture was reacted at 165° C. with stirring at 300 rpm using a pitched-paddle type impeller. Samples were withdrawn from the reactor periodically and examined for evidence of crystallisation.

After 424.5 hours at reaction temperature the preparation was crash cooled to ambient temperature and the product discharged. The product was filtered, washed with demineralised water and dried at 110° C.

Figure 7:
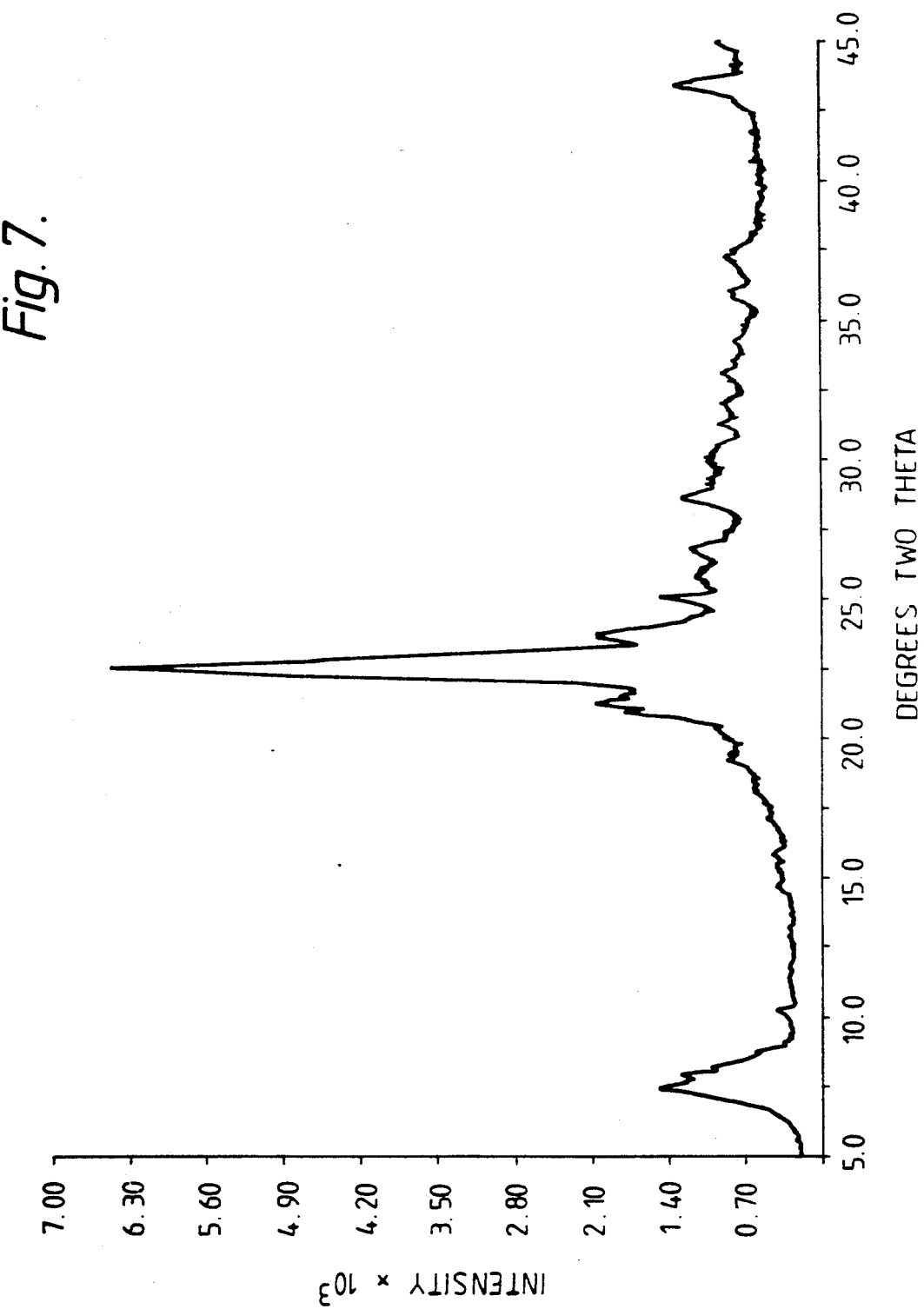
FIG. 7 is the X-ray diffraction pattern of the product of Example 10.

The product was analysed by X-ray powder diffraction and identified as NU-86. The diffraction pattern is given in FIG. 7.

EXAMPLE 11: PREPARATION OF H-NU-86

A portion of the material from Example 10 was heated under a flow of nitrogen gas for 24 hours at 450° C. followed by 16 hours at 550° C.

The resulting material was then contacted for 2 hours, at 60° C., with a 1 molar solution of ammonium chloride, using 10 ml of solution per gram of zeolite. The solid product was filtered, washed, dried and then the ion-exchange procedure repeated. The material was then calcined, in nitrogen, for 16 hours at 550° C. The resulting NH$_4$-NU-86 was filtered, washed and dried. Finally the product was heated under a flow of nitrogen gas for 16 hours at 550° C.

Analysis for Si, Al and Na revealed the following molar composition:

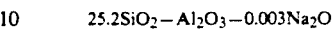

$25.2SiO_2 - Al_2O_3 - 0.003Na_2O$

Figure 8:
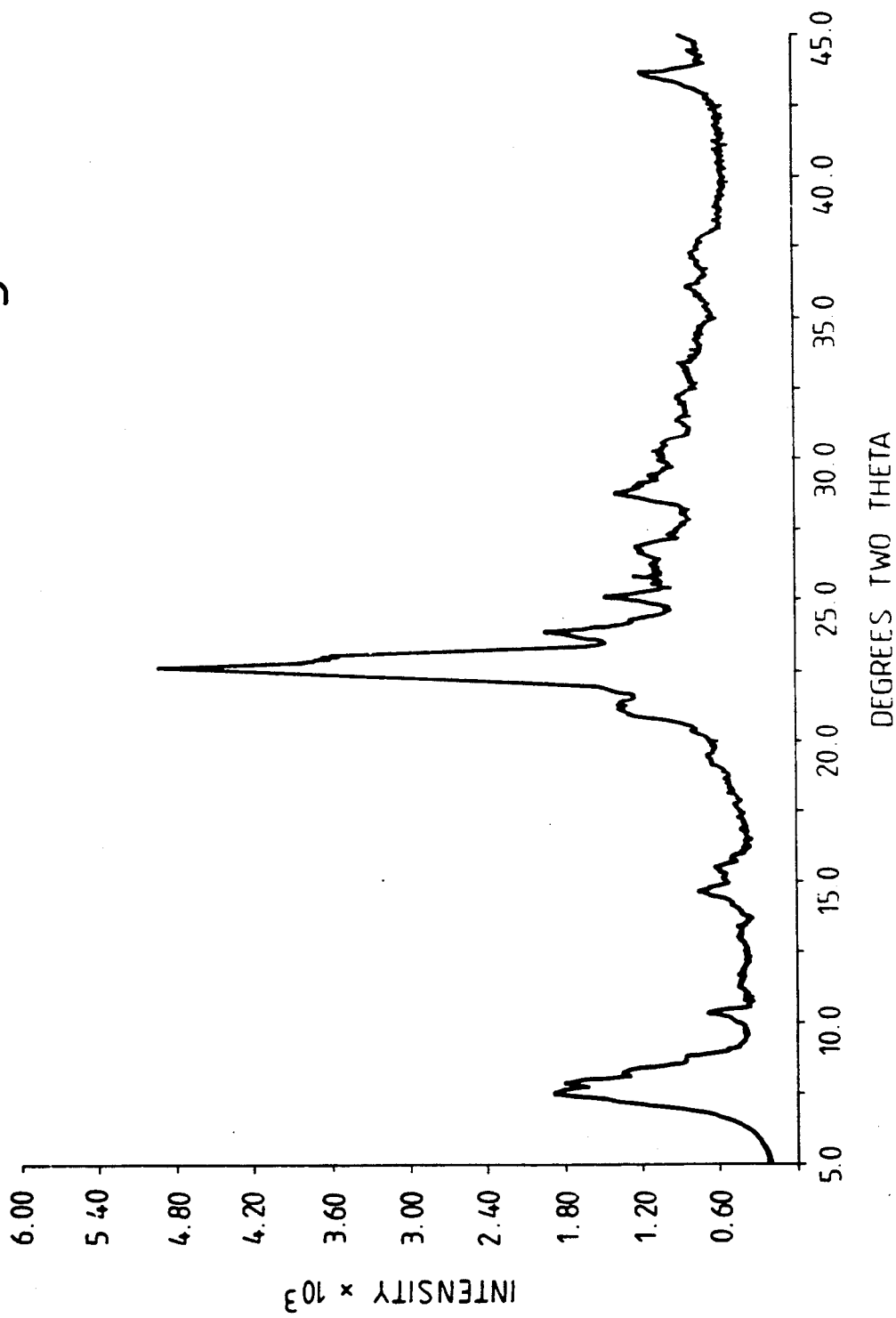
FIG. 8 is the X-ray diffraction pattern of the product of Example 11.

The product was analysed by X-ray powder diffraction and identified as H-NU-86. The diffraction pattern is given in FIG. 8 and the interplanar spacings and intensities in Table 10.

The invention relating to catalysts comprising NU-86 and processes using these catalysts is illustrated by the following Examples.

EXAMPLE 12: CRACKING OF N-BUTANE

The cracking of n-butane over H-NU-86 was examined using a portion of the material from Example 3. The procedure followed that described by: H Rastelli Jr., BM Lok, J A Duisman, D E Earls and J T Mullhaupt, Canadian Journal of Chemical Engineering, Volume 60, February 1982, pages 44–49, the contents of which are incorporated herein by reference.

A portion of the product from Example 3 was pelleted, broken down and sieved to give a 500–1000 micron size fraction. 0.449 g of this material was charged to a stainless-steel micro reactor (internal diameter 4.6 mm) and supported on glass wool and glass balls. The material was then dehydrated "in situ" by heating at 500° C. for 5 hours in stream of dry nitrogen.

A feed containing 2.19% v/v n-butane, 15.36% v/v nitrogen and 82.45% v/v helium was passed over the catalyst bed. The catalyst bed was maintained at a temperature of 500° C. and at atmospheric pressure. The cracked products were analysed by gas chromatography. This showed that the zeolite cracked n-butane to C$_1$–C$_3$ hydrocarbons. At a feed flow rate of 20.7 cm$^3$ per min an n-butane conversion of 41% was measured which corresponds to a k$_A$ of 29 cm$^3$/g min, using the equation given in the above reference. At a feed flow rate of 50.0 cm$^3$ per min an n-butane conversion rate of 23% was measured. This corresponds to a k$_A$ of 34 cm$^3$/g min.

The zeolite was then regenerated by heating at 500° C. for 14.5 hours in a stream of dry air. The feed was reintroduced at a feed flow rate of 20.7 cm$^3$ per min and a n-butane conversion of 39% was measured. This corresponds to a k$_A$ of 27 cm$^3$/g min. The feed flow rate was increased to 50.0 cm$^3$ per minute and a n-butane conversion of 20% was measured. This corresponds to a k$_A$ of 29 cm$^3$/g min.

This example shows that zeolite NU-86 is an active catalyst for n-butane cracking.

EXAMPLE 13: DISPROPORTIONATION OF TOLUENE

A portion of the material from Example 3 was pelleted, broken down and sieved to give aggregates of between 425 and 1000 microns. 1 g of this material was placed in a 4 mm internal diameter stainless steel reactor and calcined at 500° C. in air for 16 hours at atmospheric pressure. The air was replaced by nitrogen and the reactor and contents were cooled to 350° C. Hydrogen was then passed through the reactor and the pressure raised to 2069 kPa. The hydrogen flow rate was set at 1728 cm$^3$ per hour, as measured at atmospheric pressure. After 1 hour, toluene was introduced into the hydrogen stream at a rate of 1.9 mls of liquid per hour. The mole ratio of hydrogen to toluene was 4 to 1 and the weight of toluene per unit weight of solid 1.64.

The compositions of the product in weight percent after 24 hours was as follows:

| Temp/ | Wt % | | | | | |
| °C. | Gas | Benzene | Ethyl-Benzene | X-ylenes | C9+ Aromatics | Conversion |
|---|---|---|---|---|---|---|
| 412 | 1.0 | 18.3 | 0.7 | 20.2 | 4.9 | 45.1 |

This shows that zeolite NU-86 is highly active and selective catalyst for the disproportionation of toluene.

EXAMPLE 14: FLUID CATALYTIC CRACKING ADDITIVE

Zeolite NU-86 was evaluated as a fluid catalytic cracking (FCC) additive by adding it in small quantities to a base FCC catalyst and then monitoring its effect on the cracking products in a microactivity test (MAT) run.

Base Catalyst

The base FCC catalyst used was Resoc-1 E-Cat (Grace Davidson). The "E-Cat" indicates that the catalyst has been deactivated on line in a FCC plant. The base catalyst was decoked by calcining in air for 24 hours at 550° C. Resoc-1 is a rare earth exchanged Ultrastabilised Y zeolite based catalyst in spray dried form.

Additive Catalyst

Each sample of NU-86 was tested by preparing two catalysts:
(a) Resoc-1, E-Cat+1% by weight fresh NU-86 based on the weight of Resoc-1, E-Cat
(b) Resoc-1, E-Cat+2% by weight fresh NU-86 based on the weight of Resoc-1, E-Cat
(the % weight of NU-86 is based on anhydrous material).

Individual catalysts were prepared by thorough physical mixing of the base catalyst with a portion of material from Example 5. The mixture was then compressed. The resulting pellet was broken up and sieved to give granules with a size in the range of 44 to 70 microns.

The feedstock used in these experiments was Cincinnati gas oil. The properties of this material are as follows.

| Vacuum Distillation | °C. |
|---|---|
| 10% at 760 mm | 312.7 (595° F.) |
| 30% | 362.8 (685° F.) |
| 50% | 407.2 (765° F.) |
| 70% | 451.7 (845° F.) |
| 80% | 501.1 (934° F.) |

The MAT runs were carried out in a fixed bed unit using a 0.897 g charge of Cincinnati gas oil and 2.5 g of catalyst. The contact time was 80 seconds. The weight hourly space velocity (WHSV) of individual runs is given in Table 11.

The catalyst samples had all been calcined in air at 538° C. for 1 hour before testing. The starting temperature for each run was 515.6° C. (960° F.).

The products were analysed by gas chromatography capillary column analysis from which the research octane number (RON) of the resulting gasoline could be determined. Table 11 lists this data.

From results given in Table 11 it can be seen that the addition of zeolite NU-86 increases the yield of $C_3$ and $C_4$ paraffins and olefins. The yield of FCC gasoline and alkylate is also increased relative to the base catalyst. (The FCC gasoline and alkylate yield is the total amount of gasoline taking into account both the quantity directly produced plus the quantity that could be made using the alkylation capacity of the olefins generated). Thus, the extra $C_3$ and $C_4$ olefins produced must more than compensate for the loss in gasoline. The zeolite NU-86 additive also increased the RON of the gasoline. Analysis of the gasoline showed that this was mainly due to increased concentration of the $C_6$ to $C_8$ aromatics (benzene, toluene, ethylbenzene and xylenes).

EXAMPLE 15: ISOMERISATION OF XYLENES

A portion of the material from Example 7 was pelleted, broken down and sieved to give aggregates of between 425 and 1000 microns in size. 0.5 g of the aggregates were placed in a 5 mm internal diameter stainless steel reactor and calcined in air for 16 hours at 500° C. and atmospheric pressure. The air was then purged with nitrogen and the reactor and contents cooled to 300° C.

A mixture of $C_8$ aromatic hydrocarbons was pumped into a vaporiser and then through the reactor at 300° C. and atmospheric pressure. Initially, the rate was 10 ml of liquid per hour. The product was analysed regularly. After 24 hours the temperature was increased to 360° C. and the feed rate reduced to 5.0 ml of liquid per hour. As the conversion fell the temperature was further increased.

The feed and product compositions obtained are given in Table 12.

The results show that NU-86 catalyses the isomerisation of xylenes with only small xylenes losses, particularly at temperatures above 400° C. Ethylbenzene loss, which is desirable for efficient xylenes isomerisation plant operation, was quite high.

EXAMPLE 16: METHYLATION OF TOLUENE

The sample of zeolite NU-86 (0.5 g) used in the previous example and still in the reactor was calcined in air for 16 hours at 500° C. The reactor was then purged with nitrogen as it was cooled to 300° C.

A mixture of toluene and methanol, in a 3 to 1 mole ratio, was pumped through the reactor at 300° C. and atmospheric pressure.

The composition of the aromatic compounds in the product at various times is given in Table 13.

EXAMPLE 17: ETHYLATION OF BENZENE

The sample of zeolite NU-86 (0.5 g) used in the previous example and still in the reactor was calcined for 16 hours at 500° C. The reactor was then purged with nitrogen and cooled to 300° C.

A mixture of benzene and ethylene, in a mole ratio of 3 to 1, was pumped through the reactor at 300° C. and 20 Bar pressure.

The compositions of the product at various times is given in Table 14.

EXAMPLE 18: HYDROISOMERISATION OF XYLENES

A sample of the material from Example 7 was pelleted, broken down and sieved to give aggregates of between 425 and 1000 microns in size. 0.1 g of the aggregates were placed in a 3 mm internal diameter stainless steel reactor and calcined in air for 16 hours at 500° C. and atmospheric pressure. The air was purged with nitrogen and the reactor and contents cooled to 300° C. Hydrogen was then introduced into the reactor and the pressure allowed to increase to 6.7 bar. The flow of hydrogen through the reactor was then set at 2.26 liters per hour.

A mixture of $C_8$ aromatic hydrocarbons was added to the hydrogen stream at a rate of 2.85 ml per hour. (The mole ratio of hydrogen to hydrocarbon was 4 to 1.) The product was analysed regularly.

Over the first 24 hours, the temperature was increased in stepwise to 400° C. As the conversion fell subsequently the temperature was further increased.

The compositions of the hydrocarbons in the feed and product are given in Table 15.

EXAMPLE 19: PROPANE AROMATISATION 1.94 g of the material from Example 11 was refluxed for 15 hours with 7 ml of a 0.1M solution of $Ga(NO_3)_3$ diluted with 120 ml of distilled water. Water was removed by rotary evaporation. The resulting powder was analysed by AAS and found to contain 2.0% by weight of gallium. The powder was pelleted, broken down and sieved to give a 500 to 1000 micron size fraction. 0.51 g of this fraction was then calcined in a stainless steel tubular reactor, under a stream of dry air at a rate of 1.5 liter per hour, at 530° C. for 8 hours.

A feed of 100% propane gas was passed over the calcined material at a pressure of 1.5 psig propane and a weight hourly space velocity of 1.83 $hr^{-1}$. The temperature was 530° C. The resulting gaseous products were analysed by gas chromatography. A gas analysis after 8 minutes on line at reaction temperature showed that 37% of the propane feed had been converted. In the gaseous hydrocarbon products, the concentration of benzene was 12.9 wt %, of toluene 14.5 wt %, and of xylene isomers 3.9 wt %. Therefore, the total concentration of aromatics in the gaseous hydrocarbon products was 31.3 wt %.

After 53 minutes on line 17.2% of the feed had been converted. In the gaseous hydrocarbon products, the concentration of benzene was 14.9 wt %, of toluene 15.9 wt % and of xylenes 5.6 wt %. Therefore, the total concentration of aromatics in the gaseous products was 36.4%.

This example demonstrates the use of gallium impregnated zeolite NU-86 in the aromatisation of propane.

EXAMPLE 20: HYDROISOMERISATION OF N-PENTANE

A slurry consisting of 1.01 g of the material from Example 7, 0.04 g of $Pt(NH_3)_4Cl_2$ and 100 ml of distilled water was stirred in a vessel at 60° C. for 6 hours.

After washing and drying, the resultant solid was calcined in a tubular furnace using dry air as follows:
a) temperature increased from 25° to 120° C. at a rate of 0.8° C. $min^{-1}$; temperature then held at 120° C. for 3 hours;
b) temperature increased from 120° to 250° C. at a rate of 0.7° C. $min^{-1}$; temperature then held at 250° C. for 3 hours; and
c) temperature increased from 250° to 450° C. at a rate of 0.6° C. $min^{-1}$; temperature then held at 450° C. for 6 hours.

After this treatment the solid was pelleted, broken down and sieved to give a 500 to 1000 micron size fraction.

(The "target loading" of platinum in the catalyst was 0.4% wt of platinum)

0.64 g of this material was transferred to a stainless steel reactor and reduced under a stream of hydrogen at 400° C. and a pressure of 435 psig for 17 hours. Liquid n-pentane, which had previously been dried over a molecular sieve, was vaporised and mixed with hydrogen gas to produce a mixture with a molar ratio of $H_2$ to pentane of 0.75:1. This mixture was passed over the catalyst bed at a weight hourly space velocity (WHSV) of 2.38 $hours^{-1}$ (based on the n-pentane) at a pressure of 435 psig and a temperature of 250° C. The product leaving the reactor bed was analysed by on line gas chromatography. It was found to contain 46.8% isopentane and 52.9% n-pentane and 0.23% $C_1$ to $C_4$ cracked products. This corresponds to a conversion of 37%.

This example demonstrates the use of zeolite NU-86 as a catalyst for hydroisomerisation of n-pentane.

EXAMPLE 21: PREPARATION OF AMINES

A portion of material from Example 7 was pelleted, broken down and sieved to give a 500-1000 micron size fraction. A sample of this material (1.0 g) together with 3.6 g of Versal 850 alumina, particle size in the range 500-1000 microns, was charged to a tubular stainless steel microreactor and heated to 180° C. under a flow of nitrogen before ammonia was introduced. After further heating to 300° C., methanol was introduced and conditions were adjusted to give the desired methanol conversion. The reaction products were measured by on-line gas chromatography and found to consist of a mixture of mono-, di- and tri-methylamines. After one day on stream, at a temperature of 340° C. and using a feed containing a molar ratio of ammonia to methanol of 2 at a gas hourly space velocity (GHSV) of 1100 $hr^{-1}$ the methanol conversion was 98.8% and the product consisted of 38 mole % monomethylene, 25 mole % dimethylamine and 37 mole % trimethylamine.

This example demonstrates the use of zeolite NU-86 as a catalyst for the preparation of amines.

TABLE 3

| X-RAY DATA FOR THE PRODUCT OF EXAMPLE 1 | |
|---|---|
| d/(Angstroms) | Relative Intensity |
| 11.83 | 17.3 |
| 11.12 | 11.9 |
| 10.67 | 9.6 |
| 8.63 | 4.9 |
| 8.57 | 3.4 |
| 6.08 | 1.4 |
| 5.75 | 2.6 |
| 5.56 | 11.1* |
| 4.92 | 2.9 |
| 4.83 | 3.1* |
| 4.64 | 4.2 |
| 4.24 | 19.2 |
| 4.15 | 20.8 |
| 4.11 | 21.3 |
| 3.94 | 100.0 |
| 3.88 | 53.2 |
| 3.77 | 22.6 |
| 3.74 | 24.7 |

TABLE 3-continued
X-RAY DATA FOR THE PRODUCT OF EXAMPLE 1

| d/(Angstroms) | Relative Intensity |
|---|---|
| 3.70 | 17.2* |
| 3.55 | 19.1 |
| 3.47 | 5.7 |
| 3.41 | 22.5* |
| 3.34 | 4.3 |
| 3.09 | 6.8 |
| 3.04 | 2.3 |
| 2.96 | 5.7 |
| 2.93 | 7.6* |
| 2.91 | 8.9 |
| 2.86 | 4.8 |
| 2.79 | 6.0* |
| 2.72 | 2.7 |
| 2.68 | 2.3 |
| 2.63 | 1.7 |
| 2.49 | 3.2* |
| 2.41 | 3.3* |
| 2.39 | 2.4 |
| 2.21 | 2.1* |
| 2.11 | 4.5* |
| 2.08 | 12.5 |

*The intensity of these lines may be due, in whole or, in part to the presence of analcime.

TABLE 4
X-RAY DATA FOR THE PRODUCT OF EXAMPLE 2

| d/(Angstroms) | Relative Intensity |
|---|---|
| 11.75 | 19.9 |
| 11.13 | 17.2 |
| 10.64 | 11.8 |
| 10.04 | 5.6 |
| 8.59 | 4.0 |
| 7.45 | 1.1 |
| 6.03 | 2.2 |
| 5.72 | 2.7 |
| 5.58 | 1.9 |
| 4.89 | 4.4 |
| 4.61 | 6.9 |
| 4.23 | 21.2 |
| 4.14 | 23.9 |
| 4.11 | 23.3 |
| 3.94 | 100.0 |
| 3.87 | 63.4 |
| 3.82 | 27.5 |
| 3.74 | 28.1 |
| 3.54 | 15.9 |
| 3.45 | 7.2 |
| 3.35 | 7.8 |
| 3.11 | 8.7 |
| 2.92 | 4.1 |
| 2.86 | 3.6 |
| 2.79 | 4.4 |
| 2.70 | 3.3 |
| 2.63 | 2.4 |
| 2.56 | 1.1 |
| 2.49 | 2.9 |
| 2.42 | 4.4 |
| 2.39 | 3.8 |
| 2.11 | 4.3 |
| 2.07 | 12.1 |

TABLE 5
X-RAY DATA FOR THE PRODUCT OF EXAMPLE 4

| d/(Angstroms) | Relative Intensity |
|---|---|
| 15.87 | 1.2 |
| 12.26 | 19.4 |
| 11.62 | 34.9 |
| 11 | 24.7 |
| 10.53 | 22 |
| 8.5 | 14.9 |
| 7.4 | 1.2 |
| 6.77 | 3.1 |
| 6.25 | 4.3 |
| 6.04 | 9 |

TABLE 5-continued
X-RAY DATA FOR THE PRODUCT OF EXAMPLE 4

| d/(Angstroms) | Relative Intensity |
|---|---|
| 5.81 | 4.5 |
| 5.66 | 7.1 |
| 4.84 | 2.1 |
| 4.58 | 4.3 |
| 4.38 | 5.7 |
| 4.21 | 19.9 |
| 4.13 | 17.6 |
| 4.06 | 21.6 |
| 3.93 | 100 |
| 3.84 | 56 |
| 3.73 | 30.9 |
| 3.67 | 21.3 |
| 3.54 | 29 |
| 3.45 | 13.1 |
| 3.39 | 17 |
| 3.3 | 10.6 |
| 3.28 | 8.8 |
| 3.11 | 15.9 |
| 2.95 | 12.7 |
| 2.91 | 14.2 |
| 2.84 | 10.6 |
| 2.81 | 9.5 |
| 2.77 | 12.8 |
| 2.71 | 6.9 |
| 2.68 | 8.3 |
| 2.62 | 5.7 |
| 2.58 | 5 |
| 2.53 | 4.6 |
| 2.47 | 5.6 |
| 2.37 | 4.3 |
| 2.33 | 1.7 |
| 2.3 | 1.8 |
| 2.257 | 1.5 |
| 2.071 | 13.2 |
| 2.067 | 12.2 |
| 2.01 | 3.3 |

TABLE 6
X-RAY DATA FOR THE PRODUCT OF EXAMPLE 5

| d/(Angstroms) | Relative Intensity |
|---|---|
| 11.68 | 37.7 |
| 11.08 | 34.7 |
| 10.55 | 22.7 |
| 9.99 | 11.8 |
| 8.51 | 12.6 |
| 7.72 | 2.8 |
| 6.79 | 3.5 |
| 6.25 | 4.5 |
| 6.05 | 9.5 |
| 5.68 | 6.4 |
| 5.01 | 2.2 |
| 4.59 | 6.4 |
| 4.37 | 8.5 |
| 4.21 | 20.9 |
| 3.93 | 100 |
| 3.85 | 77.2 |
| 3.72 | 37.8 |
| 3.54 | 24.8 |
| 3.45 | 14.5 |
| 3.4 | 15.7 |
| 3.35 | 17.1 |
| 3.3 | 15 |
| 3.11 | 18.4 |
| 3.09 | 19.3 |
| 2.95 | 14.2 |
| 2.91 | 13.2 |
| 2.84 | 10.7 |
| 2.77 | 10.5 |
| 2.68 | 8.4 |
| 2.58 | 5.6 |
| 2.49 | 6.6 |
| 2.44 | 6.6 |
| 2.39 | 7.7 |
| 2.276 | 2.8 |
| 2.109 | 2.7 |
| 2.082 | 9.7 |
| 2.069 | 13.9 |

TABLE 6-continued

X-RAY DATA FOR THE PRODUCT OF EXAMPLE 5

| d/(Angstroms) | Relative Intensity |
|---|---|
| 2.008 | 6.7 |

TABLE 8

X-RAY DATA FOR PRODUCT OF EXAMPLE 7

| d/(Angstroms) | Relative Intensity |
|---|---|
| 25.37 | 1.3 |
| 12.65 | 16.7 |
| 11.94 | 30.9 |
| 10.75 | 21 |
| 8.65 | 14.5 |
| 7.52 | 2.9 |
| 6.89 | 3.8 |
| 6.32 | 4.6 |
| 6.1 | 9 |
| 5.73 | 6.7 |
| 4.61 | 4.6 |
| 4.39 | 6.4 |
| 4.24 | 19.1 |
| 4.16 | 18.9 |
| 4.1 | 20 |
| 3.96 | 100 |
| 3.87 | 55.9 |
| 3.86 | 46.9 |
| 3.74 | 31.3 |
| 3.7 | 21.2 |
| 3.56 | 25.8 |
| 3.47 | 13.3 |
| 3.43 | 12.4 |
| 3.32 | 11.2 |
| 3.12 | 18.1 |
| 3.09 | 15.9 |
| 2.96 | 12.3 |
| 2.93 | 14 |
| 2.86 | 12 |
| 2.78 | 11.7 |
| 2.72 | 7.4 |
| 2.7 | 7.2 |
| 2.64 | 5.6 |
| 2.59 | 5.2 |
| 2.55 | 4.2 |
| 2.51 | 3.7 |
| 2.49 | 5.5 |
| 2.46 | 3.5 |
| 2.4 | 4.7 |
| 2.3 | 1.7 |
| 2.27 | 1.2 |
| 2.164 | 1.3 |
| 2.078 | 14.3 |
| 2.041 | 2.7 |
| 2.014 | 3.6 |

TABLE 9

X-RAY DATA FOR PRODUCT OF EXAMPLE 9

| d/(Angstroms) | Relative Intensity |
|---|---|
| 22.28 | 2.7 |
| 11.82 | 34.9 |
| 10.7 | 23 |
| 8.67 | 10 |
| 7.82 | 3 |
| 7.62 | 2.8 |
| 6.86 | 3.2 |
| 6.32 | 4 |
| 6.11 | 7.9 |
| 5.71 | 6.2 |
| 4.62 | 5.2 |
| 4.24 | 18.2 |
| 4.16 | 21 |
| 3.94 | 100 |
| 3.86 | 50.2 |
| 3.73 | 28.3 |
| 3.55 | 22.3 |
| 3.46 | 13.8 |
| 3.33 | 14 |
| 3.12 | 18.6 |
| 3.11 | 19.7 |
| 2.97 | 12.25 |

TABLE 9-continued

X-RAY DATA FOR PRODUCT OF EXAMPLE 9

| d/(Angstroms) | Relative Intensity |
|---|---|
| 2.92 | 13.4 |
| 2.85 | 9.9 |
| 2.78 | 10.4 |
| 2.69 | 7.2 |
| 2.59 | 5.2 |
| 2.55 | 3.7 |
| 2.48 | 5.4 |
| 2.41 | 5 |
| 2.39 | 4.2 |
| 2.074 | 13.8 |
| 2.014 | 3 |

TABLE 10

X-RAY DATA FOR PRODUCT OF EXAMPLE 11

| d/(Angstroms) | Relative Intensity |
|---|---|
| 28.5 | 1.6 |
| 25.3 | 2.5 |
| 20.1 | 3.5 |
| 11.8 | 35.8 |
| 11.2 | 34 |
| 10.6 | 22.3 |
| 10 | 12.2 |
| 8.56 | 8.3 |
| 7.8 | 2.7 |
| 6.8 | 2.3 |
| 6.06 | 8.9 |
| 5.7 | 5.5 |
| 4.56 | 5.9 |
| 4.25 | 18.9 |
| 4.17 | 21.2 |
| 3.93 | 100 |
| 3.85 | 69 |
| 3.73 | 34 |
| 3.54 | 22.3 |
| 3.49 | 14.1 |
| 3.45 | 15.7 |
| 3.31 | 17.4 |
| 3.26 | 11.3 |
| 3.1 | 20.1 |
| 3.03 | 13.6 |
| 2.95 | 13.2 |
| 2.92 | 12.2 |
| 2.85 | 9.5 |
| 2.78 | 9.6 |
| 2.68 | 8.4 |
| 2.6 | 5.8 |
| 2.49 | 7 |
| 2.44 | 5.8 |
| 2.41 | 6.1 |
| 2.38 | 4.5 |
| 2.31 | 1.6 |
| 2.07 | 13.5 |
| 2.05 | 4.3 |
| 2.011 | 7.6 |

TABLE 11

Fluid Catalytic Cracking Additive

| Catalyst | (Comparative) Resoc-1, E-CAT | | a | b |
|---|---|---|---|---|
| WHSV (hr$^{-1}$) | 15.97 | 15.74 | 15.61 | 16.70 |
| Temperature: | | | | |
| Starting | 515.6° C. | 515.6° C. | 515.6° C. | 515.6° C. |
| lowest | 497.8° C. | 501.1° C. | 498.9° C. | 498.9° C. |
| | Wt % | Wt % | Wt % | Wt % |
| Conversion | 67.21 | 63.23.23 | 67.08 | 65.92 |
| Product Yields | | | | |
| Total C3's | 4.8 | 4.44 | 7.77 | 9.44 |
| Propane | 0.95 | 0.84 | 1.50 | 2.13 |
| Propylene | 3.86 | 3.60 | 6.27 | 7.32 |
| Total C4's | 8.89 | 8.40 | 12.21 | 13.52 |
| I-Butane | 3.58 | 3.45 | 4.92 | 5.46 |
| N-Butane | 0.66 | 0.67 | 0.99 | 1.21 |

TABLE 11-continued

| Fluid Catalytic Cracking Additive | | | | |
|---|---|---|---|---|
| Total Butenes | 4.65 | 4.29 | 6.30 | 6.85 |
| 1-Butene | 2.14 | 2.01 | 3.25 | 3.68 |
| Trans-Butenes | 1.45 | 1.31 | 1.77 | 1.83 |
| Cis-Butenes | 1.06 | 0.96 | 1.29 | 1.34 |
| BP range C5— 430° F. Gasoline | 46.10 | 44.11 | 40.17 | 36.12 |
| BP range 430–650° F. Light Cycle Gas Oil | 20.52 | 22.43 | 21.57 | 21.00 |
| BP range 650° F. and above Diesel Oil | 12.28 | 14.34 | 11.35 | 13.07 |
| FCC Gasoline + Alkylate (VOL %) | 80.57 | 76.83 | 85.61 | 85.49 |
| Research Octane Number (Gasoline) | 93.2 | 93.3 | 96.89 | 98.9 |

BP = boiling point

TABLE 12

| Isomerization of Xylenes over NU-86 | | | | | |
|---|---|---|---|---|---|
| | feed | product compositions (wt %) | | | |
| Time (hr) | | 25 | 49 | 72 | 94 |
| Temperature (°C.) | | 360 | 400 | 440 | 470 |
| Gas (wt %) | | 0.01 | 0.01 | 0.03 | 0.06 |
| Benzene (wt %) | 0.17 | 1.04 | 0.66 | 0.64 | 0.53 |
| Toluene (wt %) | 1.03 | 9.63 | 5.14 | 4.87 | 3.37 |
| Non Arom (wt %) | 0.08 | 0.08 | 0.08 | 0.07 | 0.08 |
| E Benzne (wt %) | 3.96 | 1.92 | 2.75 | 2.81 | 3.19 |
| P Xylene (wt %) | 11.89 | 16.98 | 19.52 | 19.96 | 20.67 |
| M Xylene (wt %) | 56.08 | 41.05 | 45.77 | 45.97 | 46.92 |
| O Xylene (wt %) | 25.55 | 16.92 | 19.66 | 19.65 | 21.12 |
| C9+ Arom (wt %) | 1.26 | 12.38 | 6.41 | 5.98 | 4.07 |
| % P Xylene made | | 5.09 | 7.63 | 8.07 | 8.78 |
| % Xylenes lost | | 19.85 | 9.16 | 8.48 | 5.15 |
| % E Benzene lost | | 51.60 | 30.65 | 28.93 | 19.55 |

TABLE 13

| Methylation of Toluene | | | |
|---|---|---|---|
| | Product compositions | | |
| Time (hr) | 2 | 20 | 24 |
| Feed Rate (ml/hr) | 5.0 | 5.0 | 2.0 |
| Gas (wt %) | 1.20 | 1.79 | 1.18 |
| Benzene (wt %) | 0.00 | 0.00 | 0.00 |
| Toluene (wt %) | 81.93 | 87.49 | 81.08 |
| P Xylene (wt %) | 4.00 | 2.70 | 4.02 |
| M Xylene (wt %) | 2.94 | 2.00 | 3.14 |
| O Xylene (wt %) | 5.74 | 4.40 | 6.40 |
| C9+ Arom (wt %) | 4.19 | 1.63 | 4.20 |
| Total Xylenes | 12.68 | 9.10 | 13.55 |
| % Orthoxylene in Xylenes | 45.3 | 48.3 | 47.2 |

TABLE 14

| Ethylation of benzene | | |
|---|---|---|
| | feed | product composition |
| Time (hr) | | 2 | 6 |
| Temperature (°C.) | | 300 | 300 |
| Gas (wt %) | 10.69 | 3.18 | 3.00 |
| Benzene (wt %) | 89.31 | 69.34 | 72.91 |
| Toluene (wt %) | | 0.16 | 0.16 |
| Xylenes (wt %) | | 0.67 | 0.30 |
| C9 aromatics (wt %) | | 0.66 | 0.43 |
| Ethylbenzene (wt %) | | 22.04 | 20.17 |
| Diethylbenzene (wt %) | | 3.14 | 2.32 |
| C10+Aromatics (wt %) | | 0.80 | 0.70 |
| Benzene conv (wt %) | | 22.26 | 18.26 |
| Selectivity to EB (%) | | 80.18 | 83.70 |

TABLE 15

| Hydroisomerisation of Xylenes | | | | | |
|---|---|---|---|---|---|
| | feed | Product compositions | | | |
| Time (hr) | | 23 | 31 | 73 | 94 |
| Temperature (°C.) | | 380 | 400 | 435 | 475 |
| Gas (wt %) | | 0.21 | 0.21 | 0.24 | 0.42 |
| Benzene (wt %) | 0.66 | 1.56 | 1.42 | 1.19 | 1.21 |
| Toluene (wt %) | 2.92 | 5.04 | 4.58 | 3.84 | 3.63 |
| Non Arom (wt %) | 0.49 | 1.04 | 1.04 | 1.03 | 0.90 |
| E Benzene (wt %) | 17.46 | 13.64 | 14.24 | 15.24 | 15.33 |
| P Xylene (wt %) | 7.52 | 15.77 | 16.39 | 16.71 | 16.95 |
| M Xylene (wt %) | 47.99 | 37.84 | 38.10 | 38.84 | 38.77 |
| O Xylene (wt %) | 21.51 | 17.34 | 17.63 | 18.42 | 18.75 |
| C9+ Arom (wt %) | 1.45 | 7.55 | 6.39 | 4.50 | 4.03 |
| % P Xylene made | | 8.25 | 8.87 | 9.19 | 9.43 |
| % Xylenes lost | | 7.88 | 6.36 | 3.97 | 3.30 |
| % E Benzene lost | | 21.86 | 18.43 | 12.70 | 12.19 |

I claim:

1. A zeolite, designated NU-86, having a composition expressed on an anhydrous basis (in terms of mole ratios of oxide) by the formula: 100 $XO_2$: equal to or less than 10 $Y_2O_3$: equal to or less than 20 $R_{2/n}O$ where R is one or more cations of valency n, X is silicon and/or germanium, Y is one or more of aluminum, iron, gallium, boron, titanium, vanadium, zirconium, molybdenum, arsenic, antimony, chromium and manganese and having an X-ray diffraction pattern including the lines shown in Table 1 below:

TABLE 1

| d(Angstroms) | Relative Intensity | |
|---|---|---|
| 11.8 ± 0.15 | w–m | ⎫ |
| 11.10 ± 0.15 | w–m | ⎬ (a) |
| 10.65 ± 0.15 | w | ⎭ |
| 8.60 ± 0.15 | w | |
| 4.22 ± 0.10 | m | |
| 4.15 ± 0.10 | m | ⎫ (**) |
| 4.10 ± 0.10 | w–m | ⎭ |
| 3.94 ± 0.08 | vs | |
| 3.88 ± 0.08 | s–vs | |
| 3.74 ± 0.07 | m | |
| 3.45 ± 0.06 | w | |
| 3.35 ± 0.06 | w | |
| 3.11 ± 0.06 | w | |
| 2.07 ± 0.04 | w | | where w=less than 20, m=between 20 and 40, s=greater than 40 but less than 60, vs=greater than 60, (a)=broad asymmetric reflection containing a number of peaks, the major ones of which are those occurring at d-spacings of 11.8, 11.10, and 10.65 Angstroms, and (**)=a doublet.

2. An as-prepared zeolite as claimed in claim 1 and having a composition expressed on an anhydrous basis (in terms of mole ratios of oxide) by the formula:
100 $XO_2$: less than or equal to 10 $Y_2O_3$: less than or equal to 10 Q: less than or equal to 10 $M_2O$
wherein Q is a polymethylene alpha, omega-diammonium cation having the formula:

$[(R_1R_2R_3)N(CH_2)_mN(R_4R_5R_6)]^{2+}$ where $R_1$, $R_2$, $R_3$, $R_4$, $R_5$ and $R_6$ are methyl groups, m is 8 or 9 and M is an alkali metal and/or ammonium.

3. A zeolite as claimed in claims 1 or 2 where X is silicon and Y is aluminium.

4. A zeolite as claimed in claim 1 in its hydrogen, ammonium or metal-containing forms.

5. A method for preparing zeolite NU-86 as defined in claim 1 comprising reacting an aqueous mixture comprising a source of at least one oxide $XO_2$, where X is silicon and/or germanium, at least one nitrogen-containing organic cation Q, where Q is a polymethylene alpha, omega-diammonium cation having the formula:

$$[(R_1R_2R_3)N(CH_2)_mN(R_4R_5R_6)]^{2+}$$

or a precursor thereof, where $R_1$, $R_2$, $R_3$, $R_4$, $R_5$ and $R_6$ are methyl groups and m is 8 or 9, a source of at least one oxide $Y_2O_3$, where Y is one or more of aluminium, iron, gallium, boron, titanium, vanadium, zirconium, molybdenum, arsenic, antimony, chromium and manganese, and optionally a source of monovalent cations, the mixture having the molar composition $XO_2/Y_2O_3$ at least 10

$(R_{1/n})OH/XO_2$ in the range 0.01 to 2

$H_2O/XO_2$ in the range 1 to 500

$Q/XO_2$ in the range 0.005 to 1

$L_pZ/XO_2$ in the range 0 to 5 where R is a cation of valency n which can include Q and/or M, where M is an alkali metal cation and/or ammonium, and Z is an anion of valency p and L is an alkali metal and/or an ammonium ion, and continuing the reaction until crystallisation has occurred.

6. A method as claimed in claim 5 in which the $XO_2/Y_2O_3$ ratio is at least 10 and not more than 60.

7. A method for the preparation of the hydrogen form of zeolite NU-86 comprising
 i) optionally calcining as-prepared zeolite NU-86; and
 ii) ion exchanging with an acid or with a solution of an ammonium salt.

8. A catalyst comprising zeolite NU-86 as claimed in claim 1 in which R is at least partially hydrogen.

9. A catalyst comprising zeolite NU-86 as claimed in claim 1 in which R is other than hydrogen.

10. A catalyst as claimed in claim 8 in which the hydrogen is partially or completely replaced by a metal.

11. A catalyst as claimed in any one of claims 8 to 10 further comprising a component selected from
 a) a binder;
 b) a catalyst support material;
 c) a further zeolite or a molecular sieve;
 d) a metal; and
 e) a further catalyst
or a combination thereof.

12. A process for converting an organic compound comprising contacting said organic compound under conversion conditions with a catalyst as claimed in claim 8.

13. A process for alkylation and dealkylation reactions of aromatic hydrocarbons in the presence or absence of hydrogen employing a catalyst as claimed in claim 8 said reaction being any one or more of
 a) transalkylation;
 b) disproportionation;
 c) dealkylation; and
 d) alkylation.

14. A process for isomerising a substituted aromatic compound or an aliphatic hydrocarbon in the presence or absence of hydrogen using a catalyst as claimed in claim 8.

15. A process for cracking aliphatic hydrocarbons in the presence or absence of hydrogen using a catalyst as claimed in claim 8.

16. A process for cracking a hydrocarbon feedstock to produce a high octane gasoline using a catalyst as claimed in claim 8.

17. A process for aromatisation of aliphatic hydrocarbons using a catalyst as claimed in claim 8.

18. A process for preparing amines from alcohol and ammonia using a catalyst as claimed in claim 8.

* * * * *